United States Patent
Rothenberg et al.

(10) Patent No.: US 10,900,010 B1
(45) Date of Patent: Jan. 26, 2021

(54) INCUBATOR WITH AIR CURTAIN

(71) Applicants: Barry E. Rothenberg, Del Mar, CA (US); Kyong-su Son, San Diego, CA (US); Royal Q Le, San Diego, CA (US)

(72) Inventors: Barry E. Rothenberg, Del Mar, CA (US); Kyong-su Son, San Diego, CA (US); Royal Q Le, San Diego, CA (US)

(*) Notice: Subject to any disclaimer, the term of this patent is extended or adjusted under 35 U.S.C. 154(b) by 0 days.

(21) Appl. No.: 17/011,249

(22) Filed: Sep. 3, 2020

Related U.S. Application Data

(60) Provisional application No. 62/895,587, filed on Sep. 4, 2019.

(51) Int. Cl.
| | |
|---|---|
| *B01D 46/00* | (2006.01) |
| *C12M 1/34* | (2006.01) |
| *C12M 1/00* | (2006.01) |
| *B01D 53/04* | (2006.01) |

(52) U.S. Cl.
CPC ......... *C12M 41/34* (2013.01); *B01D 46/0028* (2013.01); *B01D 46/0036* (2013.01); *B01D 53/04* (2013.01); *C12M 23/34* (2013.01); *C12M 29/24* (2013.01); *B01D 2253/102* (2013.01)

(58) Field of Classification Search
CPC ............. B01D 46/0028; B01D 46/0036; B01D 53/04; B01D 2253/102; C12M 41/34; C12M 23/34; C12M 29/24
USPC ............. 96/134, 109–114; 95/90; 435/303.1; 600/22
See application file for complete search history.

(56) References Cited

U.S. PATENT DOCUMENTS

| | | | | |
|---|---|---|---|---|
| 3,680,557 | A | | 8/1972 | Doniguian |
| 4,478,047 | A | * | 10/1984 | Ibrahim ................ F25D 21/125 62/248 |
| 4,633,677 | A | * | 1/1987 | Maehara ............... A47F 3/0447 62/256 |
| 4,936,824 | A | * | 6/1990 | Koch .................... A61G 11/006 600/22 |
| 5,169,217 | A | * | 12/1992 | Orchard .................... B01L 1/04 312/1 |

(Continued)

FOREIGN PATENT DOCUMENTS

EP    2574658 A1    4/2013

OTHER PUBLICATIONS

"Biosafety Cabinets & Clean Benches," University of New Hampshire Research Office, Copyright 2019; retrieved from the Internet at https://www.unh.edu/research/biosafety-cabinets-and-clean-benches on Jul. 8, 2019; 7 pgs.

(Continued)

*Primary Examiner* — Frank M Lawrence, Jr.
(74) *Attorney, Agent, or Firm* — Umberg Zipser LLP

(57) ABSTRACT

An incubator for cell and tissue culture under controlled atmospheric conditions has a primary air flow control device that forms a primary, preferably laminar flow, air veil across an opening that allows access to the cells or tissue cultures disposed within the incubator. Preferably, most if not all of the air in the primary (laminar flow) air veil is recirculated, and a secondary air flow control device is used that forms a secondary, preferably laminar flow, air veil between the primary (laminar flow) air veil and a user of the incubator.

20 Claims, 17 Drawing Sheets

(56) References Cited

U.S. PATENT DOCUMENTS

| | | | | |
|---|---|---|---|---|
| 5,853,361 | A | * | 12/1998 | Kobayashi .............. A61G 11/00 600/22 |
| 5,935,055 | A | * | 8/1999 | Koch ...................... A61G 11/00 600/21 |
| 6,013,119 | A | * | 1/2000 | Cecchi ............... B01D 46/0024 261/121.1 |
| 2006/0199490 | A1 | * | 9/2006 | Honda ................. A61G 11/009 454/49 |
| 2015/0050725 | A1 | * | 2/2015 | Pieczarek ............. C12M 29/26 435/303.1 |
| 2017/0280896 | A1 | * | 10/2017 | Watanabe ............. A47F 3/0478 |
| 2018/0291417 | A1 | | 10/2018 | Tipgunlakant et al. |

OTHER PUBLICATIONS

Al-Ani et al., "Oxygenation in cell culture: Critical parameters for reproducibility are routinely not reported," PLOS ONE, Oct. 16, 2018; 13 pgs.

Chen et al., "Physioxia: a more effective approach for culturing human adipose-derived stem cells for cell transplantation," Stem Cell Research & Therapy, 2018; 9:148; 12 pgs.

Mas-Bargues et al., "Relevance of Oxygen Concentration in Stem Cell Culture for Regenerative Medicine," International Journal of Molecular Sciences, 2019; 20(5),1195; 27 pgs.

* cited by examiner

Comparison of (A) temperature (within 98% of 37 °C), (B) humidity (to >90%) and (C) $CO_2$ (within 98% of 5% $CO_2$) recovery after a 30 second door opening. Different technologies produce widely varied results. Data from published brochures.
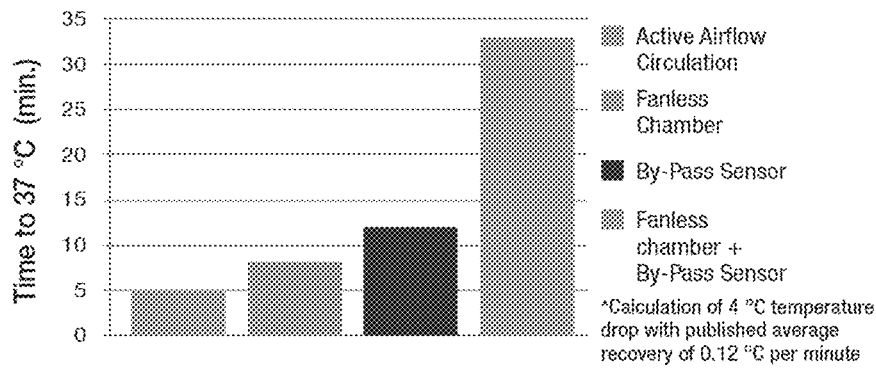
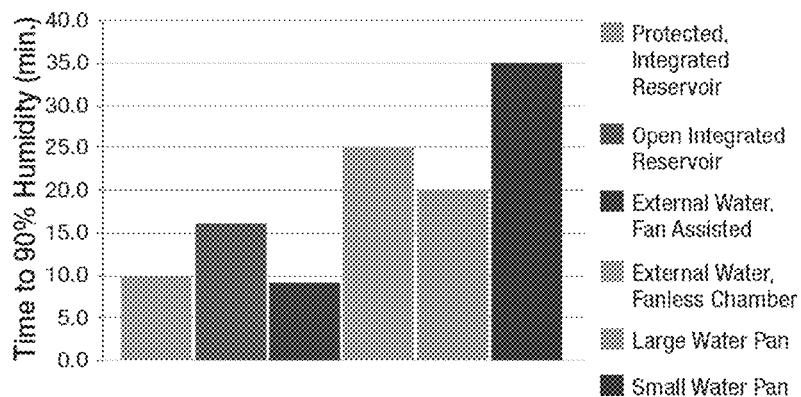
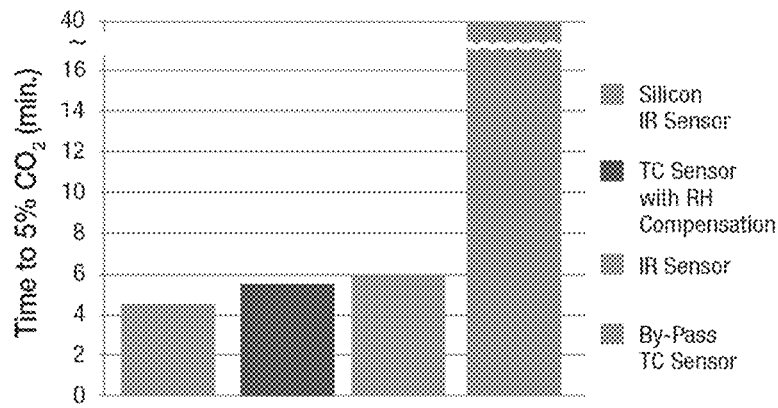
Prior Art FIG.1

INCUBATOR WITH AIR CURTAIN

This application claims priority to our provisional application with the Ser. No. 62/895,587, which was filed Sep. 4, 2019, and which is incorporated by reference herein.

FIELD OF THE INVENTION

The present disclosure is directed to devices, systems, and methods of incubators with controlled atmosphere, particularly as it relates to cell and tissue culture incubators with low-oxygen atmosphere.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As is well known, the oxygen in the atmosphere is approximately 21 vol % at sea level, and many cell and tissue culture experiments are performed without specific control of oxygen content in the cell and tissue culture incubator. As a consequence, cells and tissues grown in such incubators are exposed to oxygen levels that are not representative of physiologically normal oxygen levels in vivo. Indeed, it has been argued that all or almost all cells in a living multicellular organism exist in environments with oxygen levels that are well below atmospheric levels of oxygen (see e.g., *Int J Mol Sci*. 2019; 20, 1195; doi:10.3390/ijms20051195). For example, oxygen is typically found between 0.5-7% in the brain, between 1-5% in the eyes, between 4-12% in the liver, heart, and kidneys, and between 3-5% in the uterus. On the backdrop of the varying oxygen levels for specific cells and tissues, physiologically appropriate oxygen levels have bene termed 'Physoxia' (*Stem Cell Research & Therapy* (2018) 9:148). In addition, it has been shown that atmospheric oxygen levels in cell and tissue culture severely affect various metabolic and developmental processes. For example, 'normoxic' (i.e., 21% $O_2$) culture conditions suppress in vitro gene expression of a variety of genes, cell differentiation, proliferation, and viability of numerous stem cell lines, suppress expression of regulatory and housekeeping genes of numerous cell lines, and tend to affect metabolism and metabolic pathways of most cells.

Moreover, the significance of appropriate oxygen levels for specific cells and tissues has also been recognized in numerous studies that demonstrated that reproducibility of experiments is jeopardized or even impossible where oxygen levels in the cell cultures were not reported or suitably adjusted (PLOS ONE|https://doi.org/10.1371/journal.pone.0204269 Oct. 16, 2018). To help overcome at least some of the difficulties associated with appropriate oxygen control, incubators can be supplied with gases to adjust oxygen levels within the incubator, and a tri-gas incubator is one common variant of such devices (see e.g., Thermo Fischer Scientific, Tri-gas incubators). Here, carbon dioxide and nitrogen are fed at controlled rates into the incubator to maintain relatively constant gas conditions. Unfortunately, however, such tri-gas incubators are still subject to large oxygen excursions during operation and particularly when the incubator door is opened to add or remove a culture container. In yet another approach, modular incubator chambers can be used to more tightly control the environmental conditions (see e.g., MIC-101 by Billups-Rothenberg, Inc.). Such incubators offer a simple yet effective manner of atmospheric containment, which can be further monitored and controlled with a suitable gas mixing system and a modular oxygen monitor that can be placed within the modular incubator. However, such systems are often limited in capacity and need placement within an existing incubator for temperature control.

Compounding the above difficulties are normal operations during cell culture that require one or more culture vessels to be removed from an incubator, for example, for visual analysis and cell count, feeding or media exchange, and cell harvesting. Indeed, it is not unusual for a standard size incubator to be repeatedly opened and closed multiple times within only one or two hours. As will be readily appreciated, each time an incubator is opened, the controlled atmospheric conditions are lost and must be re-established to ensure proper culture conditions upon closing the incubator. Unfortunately, even with active airflow circulation, the time to re-establish proper temperature, humidity, and oxygen content readily exceed 5-10 minutes every time the incubator is opened as is exemplarily depicted in FIG. 1. As a consequence, the cell or tissue cultures in the incubator will experience multiple and significant deviations from the set points for the atmospheric conditions. Still further, each opening and closing cycle of an incubator will expose the entire internal volume and culture vessels to potential microbial contamination, which could jeopardize the entire contents of the incubator.

Thus, even though various cell culture incubators are known in the art, all or almost all of them suffer from various disadvantages. Most notably, ordinary use of the incubators will disrupt atmospheric conditions within the incubator, and re-establishment of the appropriate conditions is time consuming. Consequently, cells and tissues in the currently known incubators will be exposed to long periods of off-target conditions, changing conditions during re-establishment of the on-target conditions, and microbial contamination. Still further, conventional incubators are subject to incursion of large volumes of air upon opening the doors, leading to a substantial increase of microbial contamination. Therefore, there is still a need to provide improved incubators that provide effective atmospheric and environmental control with reduced exposure to microbial contaminants.

SUMMARY OF THE INVENTION

Incubators with effective atmospheric and environmental control are disclosed herein that use at least a primary air flow control device that directs a primary air veil along or parallel to the opening of the incubator. Most typically, a substantial portion of the air in the primary air veil is re-circulated and optionally adjusted in temperature and/or composition to accommodate changes in temperature and/or composition.

In one aspect, the inventors contemplate an incubator that has a housing that at least partially encloses an internal container, wherein the internal container has an opening. A door is coupled to the housing and/or the internal container and movable between a first position allowing access to the internal container from an outside position of the incubator and a second position preventing access to the internal container from the outside position of the incubator. Moreover, the incubator includes a primary air flow control device that is coupled to the housing and/or the internal container and that directs a primary air veil along or parallel to a hypothetical plane covering the opening.

In some contemplated aspects, the incubator also includes a secondary air flow control device that is coupled to the housing and/or the internal container to direct a secondary air veil substantially parallel to the primary air veil. Moreover, it should be appreciated that contemplated incubators will preferably also include a primary and/or secondary suction fan, wherein the primary suction fan is positioned to receive air from the primary air veil, and wherein the secondary suction fan is positioned to receive air from the secondary air veil. Most typically, but not necessarily, the primary air veil and/or the secondary air veil is/are a directional veil or a laminar flow veil. Additionally, it is contemplated that the primary air flow control device may also have a movable vane to at least temporarily direct (a portion or all of the) air from the primary air veil into the internal container.

In further contemplated aspects, the door of the incubator is movable in a compound motion that moves the door away and in an upward motion from the opening. Moreover, it is contemplated that the housing, the internal container, and the primary air flow control device are positioned relative to each other such as to form a recirculation space that allows for recirculation of air in the primary air veil. Advantageously, recirculation of the air in the primary air veil will recirculate at least 70%, or at least 8%, or at least 90% of the air in the veil.

Contemplated incubators may further include a filter unit, an absorber unit, a sterilization unit, a temperature control unit, a temperature sensor, a humidity sensor, an atmospheric pressure sensor, and/or a gas sensor, preferably at least partially disposed within the recirculation space. In addition, the incubator may also comprise a gas inlet through which a gas from an external source is fed to the recirculation space.

Where desired, the incubator includes a control circuit that is electronically coupled to the door, the primary air flow control device, and the secondary air flow control device. Preferably, the control circuit is programmed to operate the primary and/or secondary air flow control device, for example, once the door has started to move from the first to the second position. Furthermore, contemplated incubators may include an access control device that is programmed to receive a user command and/or validate an authorized user of the incubator, and may further be couple to a membrane filter or pressure swing adsorption unit that generates a nitrogen rich product that is delivered to the incubator as further described in more detail below.

The incubator may also include one or more trays that are movably coupled to the internal container and that have (e.g., honeycomb) channels for passage of the primary laminar flow air veil therethrough when the tray(s) is/are pulled through the first air veil. In addition, it is also contemplated that the internal container of the incubator is coupled to the housing via a movable coupling (e.g., rail or telescoping system) that allows movement of the internal container out of the housing.

Therefore, viewed from a different perspective, the inventors also contemplate an incubator that comprises a housing that at least partially encloses an internal container, wherein the internal container has an opening. Such incubator will further include a primary air flow control device that is coupled to the housing and/or the internal container that directs a primary air veil along or substantially parallel to a hypothetical plane covering the opening. Most typically, the housing, the internal container, and the primary air flow control device are positioned relative to each other to form a recirculation space that allows for recirculation of air in the primary air veil, wherein the recirculation space at least partially encloses a plurality of sensors selected from the group consisting of a $CO_2$ sensor, an $O_2$ sensor, a humidity sensor, an atmospheric pressure sensor, and temperature sensor, and further at least partially encloses a sterilization unit, a high-efficiency particulate air (HEPA) filter, an activated charcoal filter, and/or a heater.

Where desired, the incubator will also include a secondary air flow control device that is coupled to the housing and/or the internal container and that directs a secondary air veil substantially parallel to the primary air veil. Moreover, it is contemplated that the incubator may also include a primary and/or secondary suction fan, wherein the primary suction fan is positioned to receive air from the primary air veil, and wherein the secondary suction fan is positioned to receive air from the flow air veil. Preferably, but not necessarily, the secondary air flow control device is configured to receive ambient air, and the secondary suction fan expels the secondary air veil to the ambient air.

In further contemplated aspects, the primary air veil and/or the secondary air veil is/are a directional veil or a laminar flow veil, and/or the primary air flow control device recirculates at least 90% of all air in the primary air veil through the recirculation space. In some embodiments, the recirculation space at least partially encloses at least two of the $CO_2$ sensor, the $O_2$ sensor, the sterilization unit, the high-efficiency particulate air (HEPA) filter, the activated charcoal filter, and/or the heater. In other embodiments, the recirculation space at least partially encloses at least three of the $CO_2$ sensor, the $O_2$ sensor, the sterilization unit, the high-efficiency particulate air (HEPA) filter, the activated charcoal filter, and/or the heater, while in further embodiments the recirculation space at least partially encloses the $CO_2$ sensor, the $O_2$ sensor, the sterilization unit, the high-efficiency particulate air (HEPA) filter, the activated charcoal filter, and the heater. Where desired, the sterilization unit comprises a UV light source directed towards a titanium dioxide containing surface.

In still further contemplated aspects, the inventors also contemplate an incubator control unit for an incubator that has a door movable between a first position allowing access to the internal container from an outside position of the incubator and a second position preventing access to the internal container from the outside position of the incubator, and that has a primary air flow control device. In especially preferred aspects, the incubator control unit includes a microprocessor and a memory storing instructions executable on the microprocessor, wherein the instructions cause the control unit to: (a) down-regulate the primary air flow control device and optionally cause movement of a vane coupled to the primary air flow control device upon the door moving into the second position; (b) up-regulate the primary air flow control device and an optional secondary air flow control device upon the door moving into the first position; and/or (c) cause movement of a vane coupled to the primary air flow control device when the door is in the first position.

As will be readily appreciated, the control unit may be further electronically coupled to a temperature sensor, a gas sensor, an atmospheric pressure sensor, and/or a humidity sensor, and the instructions may cause the control unit to activate a heater, open a gas valve to allow entry of a gas into the incubator, and/or activate a humidifier. Additionally, or alternatively, the instructions may also cause the control unit to activate the heater, to open the gas valve to allow entry of the gas into the incubator, and/or activate the humidifier while the door is in the first position. Most typically, the gas sensor is an $O_2$ sensor and/or a $CO_2$ sensor.

In some embodiments, the control unit is further electronically coupled to an access control device that is programmed to receive a user command and/or validate an authorized user of the incubator. Most typically, the instructions cause the control unit to move the door from the first to the second position upon receiving the user command and/or validation of the authorized user. While not limiting to the inventive subject matter, the user command is a voice command or visual/gesture command. Therefore, in some embodiments the authorized user is validated by face recognition. Additionally, the control unit may also be electronically coupled to a sterilization unit, and the instructions cause the control unit to activate the sterilization unit.

In yet further contemplated aspects of the inventive subject matter, the inventors contemplate a method of maintaining a controlled atmosphere (e.g., hypoxic atmosphere) in an incubator, where such method will include a step of flowing a primary air veil along or parallel to a hypothetical plane covering an opening in an internal container of the incubator while access to the internal container is enabled from an outside position of the incubator, wherein at least 90% of air in the primary air veil is recycled through the incubator.

As noted earlier, it is contemplated that at least 90% or 95% of air in the primary air veil is recycled through the incubator. Moreover, contemplated methods may also include a step of flowing a secondary air veil substantially parallel to the primary air veil. Most typically, less than 10% of the secondary air veil is recycled through the incubator, and/or the primary air veil and/or the secondary air veil is a directional veil or a laminar flow veil. In further suitable embodiments, the primary and/or secondary air veil is formed using a plurality of primary/secondary air flow control devices. Most typically, the secondary air veil flow substantially parallel to the primary air veil, and/or the primary air veil and/or the secondary air veil is/are a directional veil or a laminar flow veil.

Further suitable methods include a step of using an incubator control circuit that controls a gas valve, a heater, and/or a humidifier, wherein the control circuit receives signals from a gas sensor, a temperature sensor, and/or a humidity sensor, wherein the gas sensor, the temperature sensor, and/or the humidity sensor sense a gas, a temperature and/or a humidity in the air that is recycled through the incubator. For example, the atmosphere is controlled such that a temperature excursion, while access to the internal container is enabled from the outside position of the incubator, is less than 5° C. In another example, the atmosphere is controlled such that a gas concentration excursion, while access to the internal container is enabled from the outside position of the incubator, is less than 2% (absolute), and in yet another example, the atmosphere is controlled such that a humidity excursion, while access to the internal container is enabled from the outside position of the incubator, is less than 5% (absolute).

Viewed from a different perspective, the inventors also contemplate a method of re-establishing a controlled atmosphere in an incubator that includes a step of allowing access to an internal container of the incubator from an outside position of the incubator through a primary air veil that extends along or substantially parallel to a hypothetical plane covering an opening in the internal container, wherein access changes the controlled atmosphere. In another step, at least some of the air in the primary air veil is recirculated through a recirculation space in the incubator while access is allowed, and in a further step at least one parameter (e.g., $O_2$ concentration, $CO_2$ concentration, humidity, and/or temperature) of the controlled atmosphere is measured in the recirculation space while the primary air veil is recirculated. Additionally, the at least one parameter can then be adjusted by injecting a gas into the recirculation space and/or heating the air in the recirculation space while the primary air veil is recirculated.

Preferably, but not necessarily, at least 90% of air in the primary air veil is recycled through the incubator, and/or the step of adjusting is performed while access is allowed. In addition, contemplated methods also allow for a step of changing a vane angle at a primary air flow control device that produces the primary air veil to enable mixing of air in the internal container of the incubator. Most typically, the primary air veil is a directional veil or a laminar flow veil. In yet further aspects of contemplated methods, at least a portion of the primary air veil may be directed into the internal container. In most cases, the controlled atmosphere in the incubator is re-established within equal or less than one minute from a maximum excursion.

In still further aspects, a method of reducing excursion of an environmental parameter of a controlled atmosphere in an incubator while opening access to an internal container of the incubator from an outside position of the incubator is contemplated. Such method will include a step of flowing a primary air veil along or parallel to a hypothetical plane covering an opening in the internal container of the incubator before opening a door to provide access to the internal container of the incubator. Upon establishing the primary air veil, the door is then moved in a compound motion that moves the door away and in a lateral motion from the opening, and upon moving the door, a secondary air veil is flowed substantially parallel to the primary air veil.

For example, at least 90% of the air in the primary air veil may be recirculated within the incubator, and equal or less than 10% of the air in the secondary air veil is recirculated within the incubator. In other examples, the flow rate of the primary air veil may be increased upon or after moving the door, or a portion of the primary air veil may be directed into the internal container of the incubator. Where desired, the primary air veil is generated by a plurality of primary air flow control devices.

In still further contemplated aspects, the inventors also contemplate a method of reducing gas (e.g., tri-gas consumption) consumption in a controlled atmosphere incubator, and such methods will include a step of feeding air, nitrogen, and/or carbon dioxide into a recirculation space in the incubator, wherein the recirculation space is fluidly coupled to a primary air flow control device. In another step, the primary air flow control device is used to flow a primary air veil along or substantially parallel to a hypothetical plane covering an opening in an internal container of the incubator while access to the internal container is enabled from an outside position of the incubator. Most typically, at least 90% or 95% of air in the primary air veil is recycled through the incubator.

While not limiting the inventive subject matter, it is generally preferred that the primary air veil is a directional veil or a laminar flow veil, and/or that a secondary air veil is flowed substantially parallel to the primary air veil. In some embodiments, the nitrogen is provided from a membrane filter or pressure swing adsorption unit, and most typically, the controlled atmosphere is a hypoxic atmosphere.

Moreover, the inventors also contemplate a gas supply system for a controlled atmosphere incubator that includes an ambient air compressor that is fluidly coupled to a gas mixing unit via a first conduit, a second conduit coupling the ambient air compressor to a pressure swing absorption (PSA) unit or a membrane filtration unit, wherein the PSA or membrane unit produces a nitrogen rich product. Most typically, the second conduit further couples the PSA or membrane unit to the gas mixing unit, and a third conduit couples the gas mixing unit to the controlled atmosphere incubator. Where desired, the gas supply system will also include a source of compressed $CO_2$ fluidly coupled to the gas mixing unit via a fourth conduit.

In preferred aspects, the first, the second, the third, and/or the third conduit will include a flow control valve and/or a mass flow meter. Most typically, the gas supply system will also have an $O_2$ and a $CO_2$ sensor downstream of the gas mixing unit. Preferably, the first and/or the second conduit will comprise a surge tank, and/or the third conduit is fluidly coupled to a reservoir upstream of the controlled atmosphere incubator. Additionally, it should be appreciated that in gas supply systems contemplated herein the third conduit is fluidly may be coupled to a second reservoir upstream of a second controlled atmosphere incubator.

In yet further embodiments, the inventors also contemplate an incubator that has a housing that at least partially encloses an internal container (typically having a volume of between 10 and 200 L), wherein the internal container has an opening. A primary air flow control device is coupled to the housing and/or internal container and positioned relative to the internal container to direct a primary air veil along or substantially parallel to a hypothetical plane covering the opening, and a secondary air flow control device is coupled to the housing and/or internal container and positioned relative to the internal container to direct a secondary air veil parallel to the primary air veil. Additionally, a door is coupled to the housing and/or internal container such that the entire door is movable away from the hypothetical plane and such that the entire door is moveable in a horizontal or vertical direction.

In some embodiment, the internal container, and the primary air flow control device are positioned relative to each other to form a recirculation space that allows for recirculation of air in the primary air veil. Most typically, the recirculation space encloses at least partially a plurality of sensors (e.g., $CO_2$ sensor, $O_2$ sensor, humidity sensor, atmospheric pressure sensor, and/or temperature sensor), and may further at least partially enclose additional functional components (e.g., sterilization unit, high-efficiency particulate air (HEPA) filter, activated charcoal filter, and/or a heater).

Where desired, the incubator may also include a primary and/or secondary suction fan, wherein the primary suction fan is positioned to receive air from the primary air veil, and wherein the secondary suction fan is positioned to receive air from the flow air veil. In further embodiments, the secondary air flow control device may be configured to receive ambient air and the secondary suction fan expels the secondary air veil to the ambient air.

Typically, but not necessarily, the primary air veil and/or the secondary air veil is a directional veil or a laminar flow veil. In additional embodiments, the primary air flow control device recirculates at least 90% of all air in the primary air veil through the recirculation space and/or may further comprise or be coupled to a movable vane that controls the direction of the primary air veil. In still further embodiments, the primary and/or secondary air veil has an airflow between about 0.3 to 0.6 m/s Additionally, it is contemplated that the incubator may include a control unit having a microprocessor and a memory storing instructions executable on the microprocessor, wherein the instructions cause the control unit to: a) down-regulate the primary air flow control device and optionally cause movement of a vane coupled to the primary air flow control device upon the door moving into a closed position; b) up-regulate the primary air flow control device and an optional secondary air flow control device upon the door moving into an open position; and/or c) cause movement of a vane coupled to the primary air flow control device when the door is in the open position. Where desired, the control unit may further be electronically coupled to a temperature sensor, a gas sensor, an atmospheric pressure sensor, and/or a humidity sensor, and the instructions may cause the control unit to activate a heater, open a gas valve to allow entry of a gas into the incubator, and/or activate a humidifier. Moreover, the control unit may be electronically coupled to an access control device that is programmed to receive a user command (e.g., voice command or user gesture) and/or validate an authorized user (e.g., by face recognition) of the incubator, and the instructions cause the control unit to move the door from the closed to the open position upon receiving the user command and/or validation of the authorized user.

In still further embodiments, the door, when in a closed position, may be positioned in an area otherwise occupied by the secondary air veil (with the secondary air veil not operating).

Various objects, features, aspects, and advantages will become more apparent from the following detailed description of preferred embodiments, along with the accompanying drawing in which like numerals represent like components.

BRIEF DESCRIPTION OF THE DRAWING

FIG. 1 depicts exemplary graphs for recovery of selected environmental parameters of known incubators.

DETAILED DESCRIPTION

Figure 2:
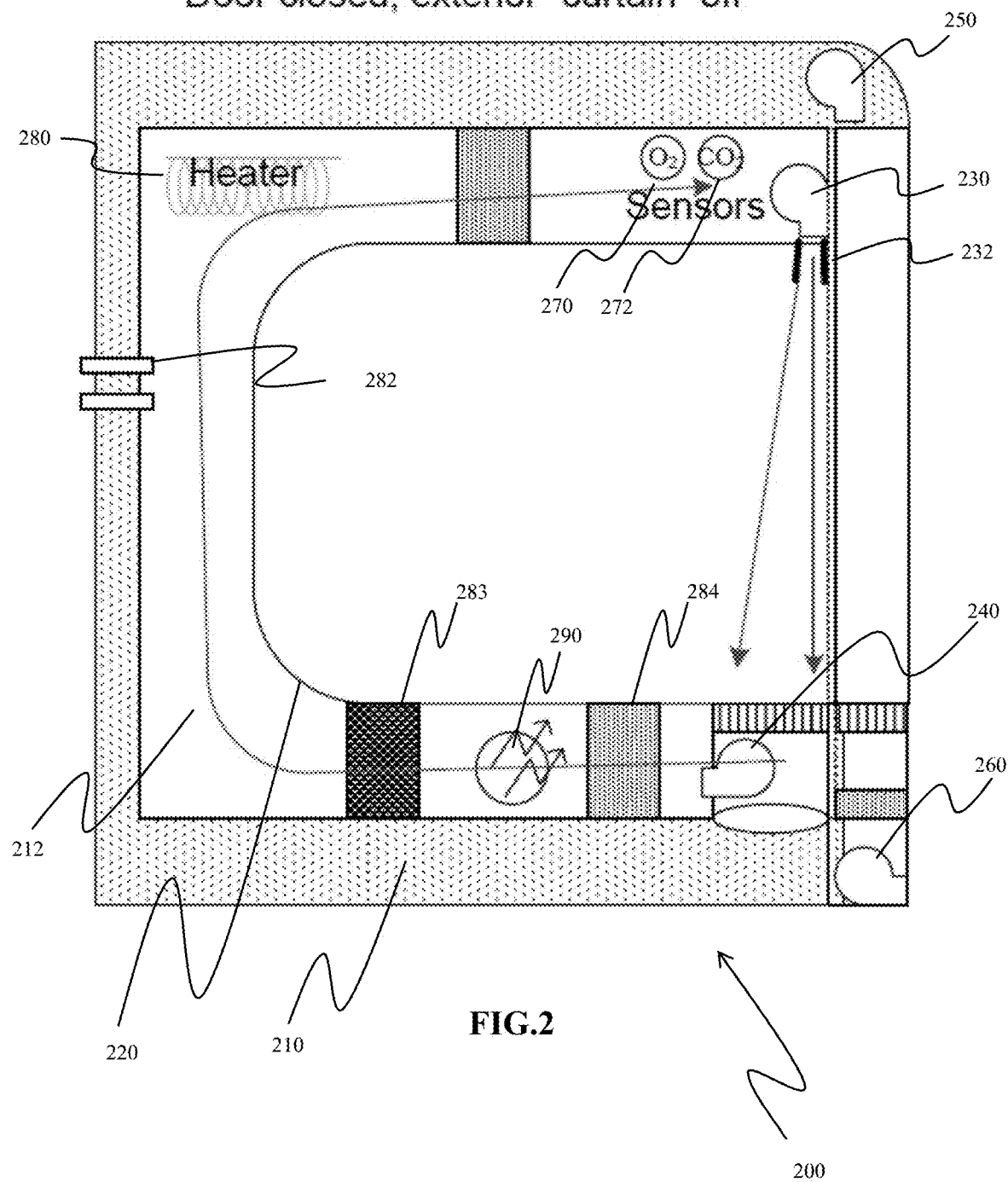
FIG. 2 depicts an exemplary view of schematic airflow in an incubator with closed door according to the inventive subject matter.

The inventors have now discovered that cell and tissue culture incubators can be manufactured and operated in a conceptually simple yet effective manner that provides superior atmospheric and environmental control. Indeed, the incubators presented herein have demonstrated a heretofore unobtainable operational stability with respect to controlled atmospheric conditions within the incubator, even when the incubator is opened and a user interacts with content within the incubator. Such operational benefits are achieved by use of one or more air veils that are directed along or substantially parallel to a hypothetical plane covering the opening wherein a significant portion of the air in the air veil is recirculated. Moreover, the composition, flow rate, and/or temperature or the air in the air veil can be adjusted in real-time, and where desired, a portion of the air veil can be directed into the incubator (e.g., using a movable vane) to replace or supplement air lost form the inside of the incubator.

In contrast, it should be appreciated that contemplated incubators and methods therefor presented herein are significantly distinct from known laminar flow sterile hoods, laminar airflow workstations, or biosafety cabinets where the air within the entire chamber is subject to vertical flow. While such devices will protect the cells or material that is within the chamber, such devices are unsuitable for cell and tissue culture as these which devices will fail to maintain operational parameters within the tight requirements of cell or tissue culture. Most typically, air is drawn into these devices, filtered, and then exits the device without providing any significant control (e.g., maintenance of hypoxic conditions for stem cell cultures). Viewed from a different perspective, air flow in such laminar flow cabinets is a single pass flow through.

Therefore, and in a more general aspect of the inventive subject matter, the inventors contemplate an incubator that has a housing that at least partially encloses an internal container, wherein the internal container is sized and dimensioned to accommodate cell or tissue culture containers, and wherein the internal container has an opening through which cell or tissue culture containers can be placed into or removed from the internal container. Most typically, a door is coupled to the housing and/or the internal container and movable between an open (first) position that allows access to the internal container from the outside of the incubator and a closed (second) second position that prevents access to the internal container from the outside. Where desired, the housing and/or doors may also include EMI shielding to prevent interference of electromagnetic radiation with the incubator, associated equipment, and/or cells or tissues in the incubator.

As will be readily appreciated, the size, dimensions, and volume of the internal container may vary considerably, and the particular use will at least in part determine these dimensional parameters. Most typically, the internal container will be sized and dimensioned in accordance with currently known cell and tissue culture incubators. Thus, the volume of the internal container may vary depending on specific demands and will typically be between 10-30 L, or between 30-50 L, or between 50-150 L, or between 100-200 L, or between 150-300 L, and even larger. Most typically, the incubators presented herein will be used as cell or tissue culture incubator, but in other embodiments, the devices presented herein can also be configured as an incubator shaker, refrigerator, freezer, workbench, gloveless glovebox, etc. Thus, suitable volumes will be at least 10 L, or at least 20 L, or at least 50 L, or at least 100 L, or at least 150 L, or at least 200 L, or even more.

A primary air flow control device is then coupled to the housing and/or the internal container that directs a primary air veil along or parallel to a hypothetical plane covering the opening. In this context, it should be noted that the phrase "along or parallel to a hypothetical plane covering the opening" is intended to express that the air veil will extend across substantially all of the opening (e.g., at least 85% or at least 90% or at least 95% of the opening). Likewise, where the air veil is substantially parallel to the hypothetical plane, the angle between the hypothetical plane and the air veil will be less than 30 degrees, or less than 20 degrees, and less than 15 degrees, or less than 10 degrees. Consequently, the air veil may be placed in front of the opening, behind the opening, and/or within the opening. Moreover, it should be recognized that the air veil need not be a sheet-like structure having uniform thickness but may also be configured as an air veil that has a thinner portion on one end and a wide portion on the other end. Moreover, and as is described in more detail below, the air veil may also be a composite veil from multiple individual veil portions that act in concert as a single veil.

While not limiting to the inventive subject matter, it should be appreciated that the incubator may also comprise a secondary air flow control device that is coupled to the housing and/or the internal container and that directs a secondary air veil substantially parallel to the primary air veil. Once more, it should be noted that the phrase "secondary air veil substantially parallel to the primary air veil" is intended to express that the two air veils do not intersect, have a distance between them, and may be therefore be at an angle relative to each other (less than 30 degrees, or less than 20 degrees, and less than 15 degrees, or less than 10 degrees). Typically, the second air veil will be of uniform thickness, but it is also contemplated that the second air veil may be thinner on one end and thicker on another end.

In still further contemplated aspects, it should be recognized that the primary and secondary air veils are both preferably oriented in a top-down flow direction, or have a flow in the same direction (e.g., both side-to-side). However, in less preferred aspects, the air veils need not be directed in the same orientation. Regardless of the orientation, it is typically preferred that the air veils are generated by primary and/or secondary air flow control devices, and most preferably by tangential fans, air jets, and/or regular fans. As needed or desired, the airflow may be further directed through one or more devices (e.g., honeycomb structure, cylindrical structures that may or may not constrict, multiple blades or vanes, etc.) to assist in non-turbulent (directional or laminar) air flow. While not limiting to the inventive subject matter, it is further contemplated that the primary and/or secondary air flow control devices will be assisted by primary and/or secondary suction fans to help stabilize the air veils. Accordingly, in preferred aspects of the inventive subject matter, the primary suction fan will be positioned to receive air from the primary air veil, and the secondary suction fan will be positioned to receive air from the secondary air veil. In further preferred aspects, the primary air veil and/or the secondary air veil may therefore be directional veils and/or a laminar flow veils. In yet further contemplated devices, the air veils may also be formed by counterrotating fans producing a directional non-laminar flow.

As noted earlier, it is generally preferred that a substantial portion of the air in the primary air veil is recirculated through the incubator. While possible, such recirculation is typically not implemented (or even necessary) for the secondary air veil. Accordingly, the air for the secondary air veil may be drawn from a location outside of the incubator and may be vented via the secondary suction fan to another location outside of the incubator. In at least that sense, first and second air veils and primary and/or secondary air flow control devices will/can be operated independently. In addition, it is generally contemplated that at least the primary air flow control device will include a mechanism (e.g., a movable vane) that provides control over the direction and/or geometry of the primary air veil. As will be discussed in more detail below, such control is particularly advantageous where a portion of the primary air veil is directed into the internal container to rapidly adjust one or more atmospheric parameters (e.g., temperature, gas concentration, humidity, etc.) in the internal container.

Moreover, it should be appreciated that recirculation of the air from the primary air veil though a recirculation space will allow for rapid adjustment of one or more parameters of the recirculating air (e.g., gas composition, temperature, humidity, etc.), and with that environmental control within the incubator. Most typically, the recirculation space will be formed by a space between the housing and the internal container that will most typically include several additional devices and/or sensors for control and/or adjustment of the one or more parameters of the recirculating air. For example, a filter unit (e.g., HEPA filter), an absorber unit (e.g. activated charcoal filter), a sterilization unit (e.g. UV based sterilization unit), a temperature control unit (e.g. heater), a temperature sensor, a humidity sensor, an atmospheric pressure sensor, and/or a gas sensor (e.g. $O_2$ and/or $CO_2$ sensor) may be disposed within the recirculation space. Moreover, one or more gas inlets may be provided to the recirculation space through which gas(es) from an external source can be fed to the air in the recirculation space. However, as shown in more detail below, the recirculation space may also be configured as a separate space/volume that is fluidly coupled to the internal container.

In some embodiments contemplated incubators use distinct spaces (e.g., an outer recirculation space and internal container) to separate the air volume in the inner container from the air volume outside the inner container. In practice, it is not necessary for the recirculation space to wrap around the internal container as shown in the exemplary incubator of FIGS. 6, 8, and 9. Indeed, it is contemplated that any configuration which maintains the same primary and/or secondary air flow control devices will work, including side-by-side, and piped designs. However, one significant benefit of the wrap-around design as shown is that as the air volume circulates, the air will exhibit centrifugal behavior, which will cause particles to preferentially stay near the outside edges of the recirculation space, forcing them to pass through and be caught by the filtration system built into recirculation space. In addition, any unmetered air entering the enclosure through the opening will also be caught and sent through the recirculation space to be conditioned, allowing for lower environment transients in the internal container. Another benefit of contemplated configurations is for ease of maintenance (e.g. filter exchanges) during operation.

With respect to suitable doors it is contemplated that any door that can at least temporarily close the opening is deemed suitable for use herein, and contemplated doors can provide access to the internal container by a rotating/pivoting motion (e.g., around a hinge), vertical or horizontal translating motion (e.g., using telescoping gear), or a compound motion (e.g., using trammel or compound pivot). However, it is generally preferred that the door is coupled to the housing and/or the internal container in a manner such that the door moves the door (first) away and (then) in an upward motion from the opening. Such manner of opening will advantageously reduce the severity of air motion forcing air from the inside of the incubator to the outside and/or the amount of turbulent air between the door and the inside of the incubator chamber. For example, the door will preferably be movable in a non-pivoting motion (not on a hinge or other pivoting mechanism extending along one edge of the door), typically in a first movement along a Y-axis (towards or away from the internal container) and a second movement parallel to a hypothetical plane extending across the opening (X- or Z-axis). Such movements are preferably sequential or may be performed in a single compound motion. Alternatively, the door may also be rotated about an axis that is near, at, or outside the perimeter of the door (typically after first moving the rotating door away from the opening). In further embodiments, the door may also be configured as a flexible or segmented cover with each segment coupled to the next via a flexible connector or film (thus being similar to a segmented garage door). Such flexible or segmented door can be moved in a sliding motion substantially parallel to the opening and towards a top or side wall of the internal container or housing.

In addition, it should be noted that the door may also use a use magnetic (or mechanic) door seal to accommodate pressure differences between the inside and outside of the incubator. Where desired, it is further contemplated that the door may include a safety mechanism that is designed to prevent closing onto a shelf or an operator, and suitable safety mechanisms may be based on torque increase, optical sensors, and/or proximity sensors, all of which are well known in the art. Notably, it should be appreciated that contemplated incubators need not have a door at all so that the so modified incubators can be used as a glove box, a (biosafety level 2+) cell or tissue culture bench, as a fume hood, etc. Thus, it should be appreciated that the opening of the internal container is shielded by dual air curtains/veils. Advantageously, such shielding significantly reduces, or even entirely avoids contamination avoided due to a lack of contaminated air pushing or being sucked into the internal container as is common with heretofore known incubators.

Viewed from a different perspective, the air veil(s) act as a virtual air-lock that prevents contamination while preserving the environment of the internal container.

As will be readily appreciated, the operation of contemplated incubators will preferably be controlled via a preprogrammed and/or programmable control circuit that will typically also be configured to informationally communicate with various external devices (e.g., smart phones, tablets, network nodes or access points, etc.). In typical aspects, the control circuit will electronically coupled at least to the door, the primary air flow control device, and/or the secondary air flow control device, and most typically also to a temperature sensor, a gas sensor (e.g., $O_2$ sensor or a $CO_2$ sensor), an atmospheric pressure sensor, and/or a humidity sensor, and wherein the control circuit is programmed to activate a heater, open a gas valve to allow entry of a gas into the incubator, and/or activate a humidifier as is described in more detail below. Still further, it should be appreciated that the control circuit may be electronically coupled to an access control device that is programmed to receive a user command (e.g., voice command) and/or validate (e.g., via image recognition) an authorized user of the incubator, and that the control circuit will open and/or close the door upon receiving the user command and/or validation of the authorized user.

For example, suitable sensors include $CO_2$ and $O_2$ gas sensors (note that the $N_2$ concentration can be derived from sensed $CO_2$ and $O_2$ concentrations), temperature sensors, humidity sensors, and air pressure sensors. In preferred embodiments, sensors for each environmental parameter are present in triplicate to avoid "split-brain" sensing errors, and the sensors can be placed in strategic locations in the airpath to allow faster response and more precise control. It should further be appreciated that sensors used in contemplated incubators can be divided into nominal "fast" and "precision" categories. The fast sensors achieve reasonably accurate real-time results (generally under a second), while precision sensors may take up to 15 seconds to settle but provide a "calibration" level of accuracy. An example of fast sensors are thermocouples which can be commonly sourced with typical accuracies ranging from 0.5 deg C. to 5 deg C. (depending on model) and with a typical response time within a tenth of a second. Examples of precision sensors are Platinum RTD (Resistance Temperature Detector) sensors, which are generally available with accuracies from 0.1 deg C. to 1 deg C. and with settling times ranging from 1 to 30 seconds.

In normal stable closed loop operation, the precision sensors are used to maintain very precise control of the operating environment. When environment perturbations are detected (e.g., the door is opened), the incubator uses the fast sensors to rapidly access and correct for any detected deviations. Once deviations settle, the incubator reverts back to the precise sensors for control. For example, temperature control can be provided by a thermoelectric module located on the rear of the recirculation space that can provide heating (and moderate cooling, if the ambient is above 37 deg C.) capabilities. Oxygen/Nitrogen control can be provided by either a nitrogen tank as is well known in the art plus filtered compressed air or via a specialty mixed gas generator. $CO_2$ is generally provided from a gas tank as is well known in the art. For humidity control, it is contemplated that the unit can use technologies ranging from the well-known traditional heated pan to dedicated humidity control technologies such as molecular sieve adsorption for humidity reduction and external humidity generators for humidity increase. Optionally the unit can also control for precise air pressure, typically by feeding or bleeding gases into or from the incubator.

FIG. 2 depicts a side view of an exemplary configuration and airflow in an incubator with the closed door. In this exemplary view, it should be recognized that the door is in a closed position with only the primary air control in operation (air flow is indicated by the arrows). As will be appreciated, environmental control of the atmosphere in the internal container of the incubator 200 is maintained by recirculation of air through the primary air flow control device 230 (with movable vanes 232) through the recirculation space 212 that is formed between the housing 210 and the internal container 220. As can be seen from FIG. 2, the recirculation space includes an $O_2$ and a $CO_2$ sensor 270 and 272, a heater 280, gas inlets 282, filters 283 (activated charcoal), 284 (HEPA), and a sterilization unit 290. The air veil is formed between the primary air flow control device and the primary suction fan 240, and the air veil geometry and direction is controlled by the movable vanes 232. In this exemplary configuration, where the door is in a closed position, the air veil may be throttled down (e.g., between 50-90% of air volume flow, or between 20-50% of air volume flow, or between 20-50% of air volume flow) relative to a time where the door is opened, and the air vail my only temporarily operate where desired. The secondary air flow control device 250 and secondary suction fan 260 are turned off in this example. Moreover, it should be noted that the vanes may be moved such that at least some portion of the air of the air veil will be directed into the internal container before recirculation via the primary suction fan. Depending on the particular set points for the atmospheric parameters, it should be noted that the sensors will provide signals to the control unit (not shown) to so activate the heater, the gas inlet(s), and other devices to maintain the atmospheric parameters at the desired levels. Here, it should be especially recognized that all measurements can be performed in real time, that all corrective activities can be implemented in real time, and that the recirculation of the air through the veil and recirculation space will allow for rapid equilibration of the atmospheric parameters.

For example, recirculation rates may be adjusted such that between 0.01 and 0.1, or between 0.1 and 1.0, or between 1.0-3.0, or between 3.0-5.0, or between 5.0 and 10.0 (and even higher) internal volumes are recirculated within a time period of between 10 sec and 60 sec, or between 1 min and 5 min, or between 5 min and 15 min, or between 15 min and 1 hour. Of course, it should be recognized that these recirculation rates may vary due to specific operating conditions. For example, higher rates are typically needed where the doors are frequently opened and closed, where an operator frequently accesses the internal container, where gas concentrations need to change from one to another set point, etc. Conversely, where the doors remain closed over extended periods, the recirculation rates may be lower. Thus, the primary air flow control device may deliver an air flow of between 0.1-1 liter/min, or between 1-10 liter/min, or between 10-100 liter/min, or between 100-500 liter/min (STP). Of course, in this context it should be recognized that the recirculation volume will not only depend on the operating conditions, but also on the volume of the internal container. However, in many embodiments the volume of the internal container will be between 10-100, or between 100-200 liter, or between 200-400 liter, or between 400-1,000 liter, or between 1,000-5,000 liter, and in some cases even higher.

Figure 3:
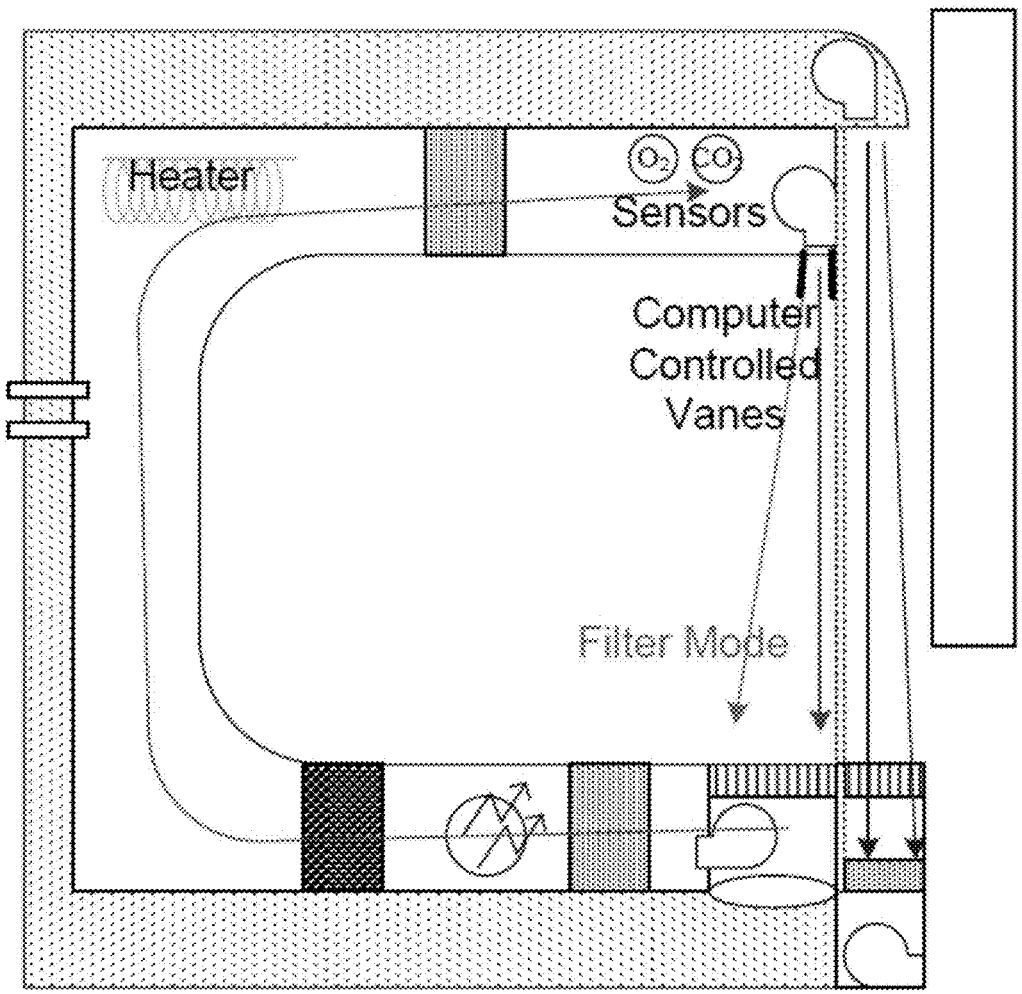
FIG. 3 depicts an exemplary view of schematic airflow in an incubator during door opening according to the inventive subject matter.
Figure 4:
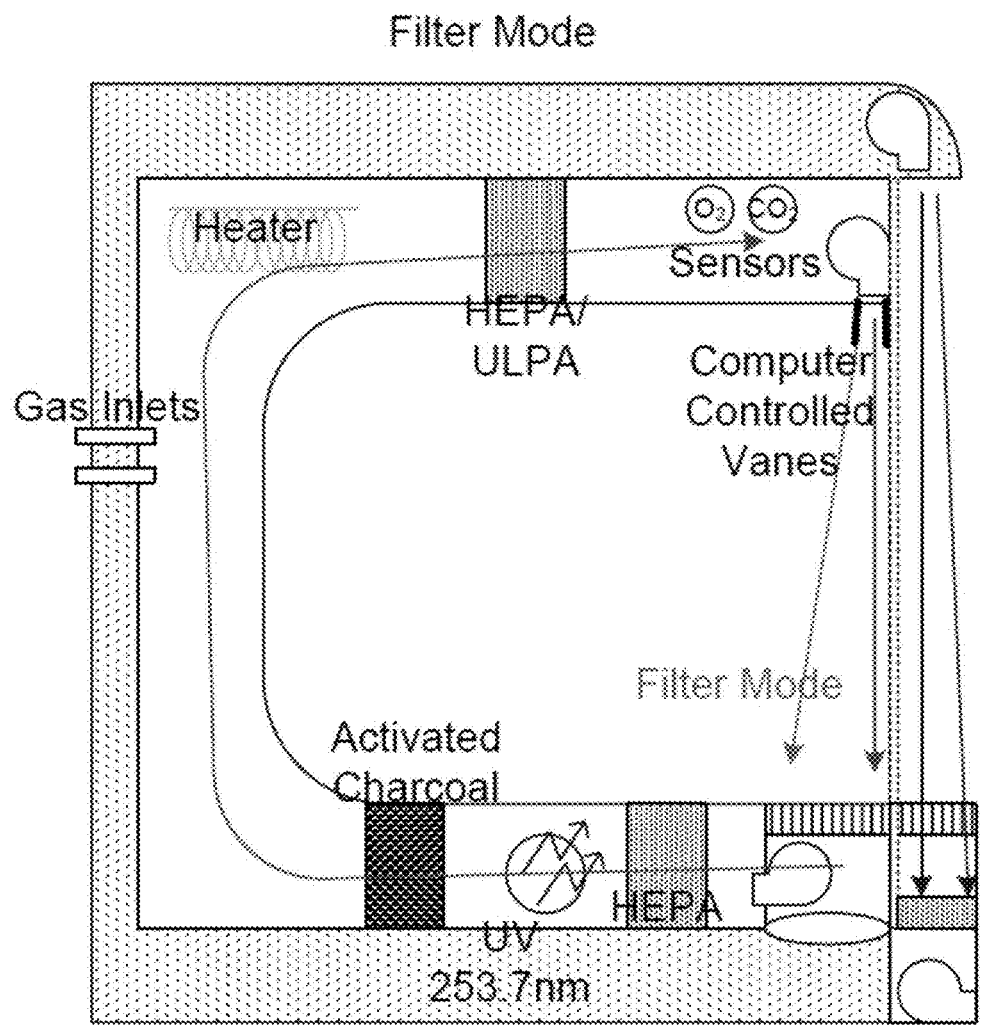
FIG. 4 depicts an exemplary view of schematic airflow in an incubator with open door according to the inventive subject matter.

Upon opening the door (e.g., in a compound motion as noted above), a secondary air veil may be established as is shown in FIG. 3. Here, the airflow is shown once more with arrows, and the secondary air veil is generated via the secondary air flow control device and the secondary suction fan. Of note, it should be appreciated that in this example the second air veil is not or substantially not (i.e., less than 10% of the air in the secondary air veil) recirculated, but vented to the outside of the incubator. While not wishing to be bound by any theory or hypothesis, it is contemplated that a secondary air veil will protect the primary air veil and establishes a first barrier against environmental disruption while the door is opening and/or opened. Moreover, where a user penetrates both air veils with his/her hands and arms, the primary and secondary air veils will cooperate to minimize environmental disruption within the interior container of the incubator. As will further be appreciated, any potential airborne contaminant will primarily enter the recirculation air stream first and be eliminated in the filters and sterilization unit. As such, the air veils will not only reduce environmental disruption but also maintain sterile operation. FIG. 4 depicts another exemplary view of airflow in an incubator with the door fully open. As is exemplarily shown, filtration and sterilization of the recirculating air is readily achieved while at the same time the primary and secondary airs help maintain the atmospheric parameters set within the internal container.

Figure 5:
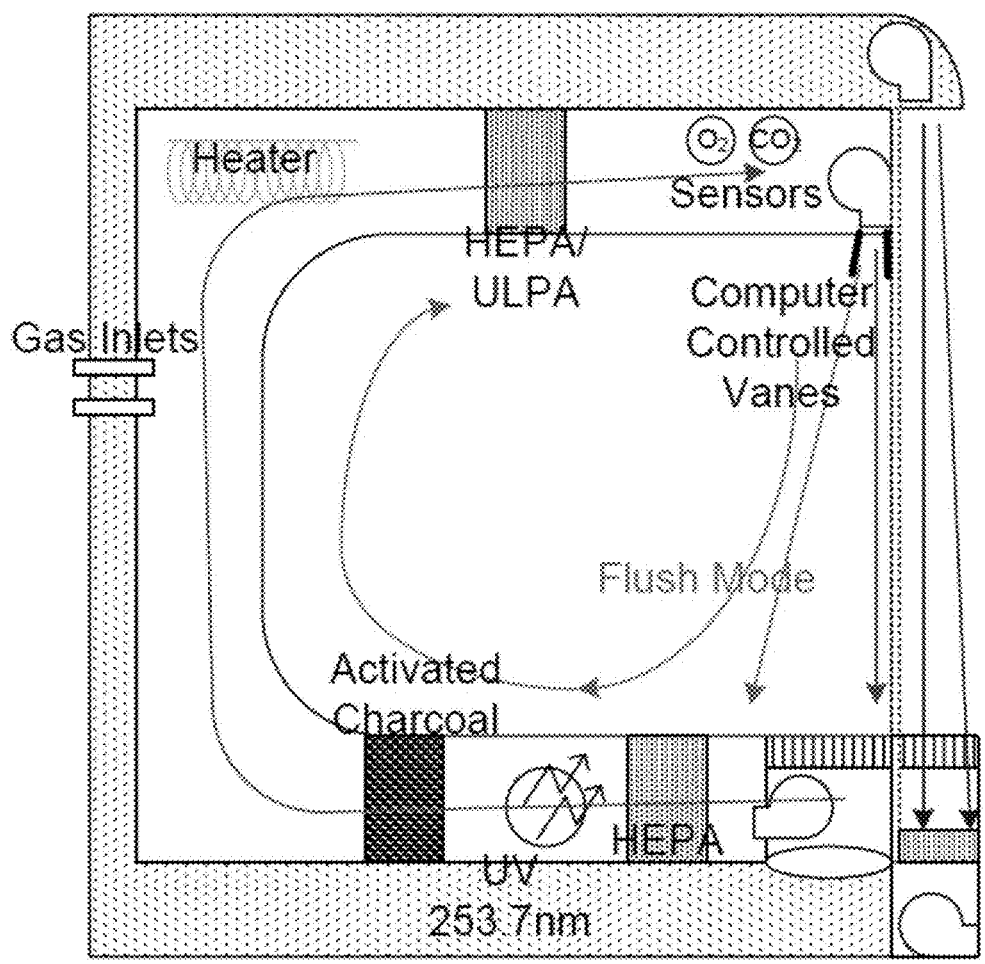
FIG. 5 depicts an exemplary view of schematic airflow in an incubator with open door in flush mode according to the inventive subject matter.

In yet a further advantageous use of the incubator components presented herein, it should be noted that any disruption in the atmospheric parameters can be corrected in real time while maintaining the primary and/or secondary air veils as is exemplarily shown in FIG. 5. Here, the vanes of the primary air flow control device are controlled to direct at least a portion of the air flow from the primary veil into the internal container before re-entering the recirculation space. Such redirection is particularly advantageous as disruptions in the atmospheric parameters measured by the sensors in the recirculation space can be corrected in real time while the door is open, and the corrections (e.g., added heat, humidity, $N_2$, and/or $CO_2$) can be implemented in real time.

With regard to the volumetric air flow in the primary and secondary air veil it should be noted that these air flows can be adjusted as needed in a flexible or pre-programmed manner. For example, where one or more sensors detect a user's hand or arm passing through the primary and/or secondary veil, the air flow can be decreased in the primary and/or secondary air veil to reduce turbulent air flow. On the other hand, where the door is opening, the air flow can be increased in the primary and/or secondary air veil in a pre-programmed manner. Alternatively or additionally, air flow rates may be modulated in a more fine-grained manner where multiple air flow control devices are implemented to produce a single air veil (e.g., reduce flow where hand or arm is detected, increase flow in others). Thus, multiple air flow control devices can be employed to generate an air veil 'around' an obstruction. In view of the above, it should therefore be appreciated that incubators according to the inventive subject matter will substantially reduce, or even eliminate variability or excursions in atmospheric parameters inside the incubator regardless of the conditions outside the incubator and even during times where a user accesses the internal container.

Depending on the particular size and configuration of the incubator, the air flow in the primary air veil and/or secondary air veil may therefore be at least 0.1 L/min, or at least 0.2 L/min, or at least 0.5 L/min, or at least 1.0 L/min, or at least 2.0 L/min, or at least 5.0 L/min, or at least 010 L/min, or at least 20 L/min, or at least 50 L/min, or at least 100 L/min. For example, typical air flow in the primary air veil and/or secondary air veil may be between 0.1 L/min and 1.0 L/min, or between 1.0 L/min and 5.0 L/min, or between 5.0 L/min and 10 L/min, or between 10 L/min and 50 L/min, or between 50 L/min and 100 L/min, or even higher.

Figure 6:
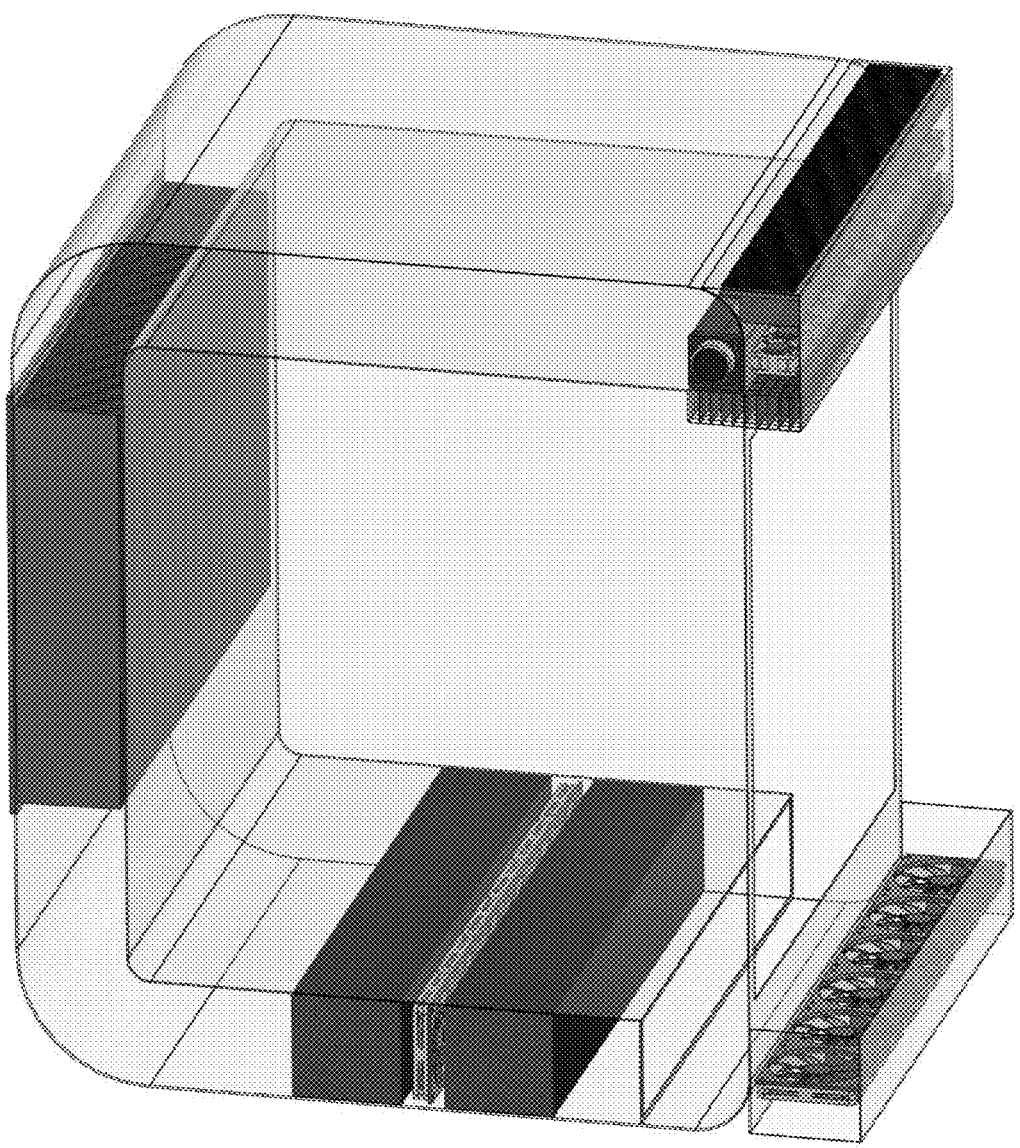
FIG. 6 depicts an exemplary view of an internal container and recirculation space showing selected components.
Figure 7:
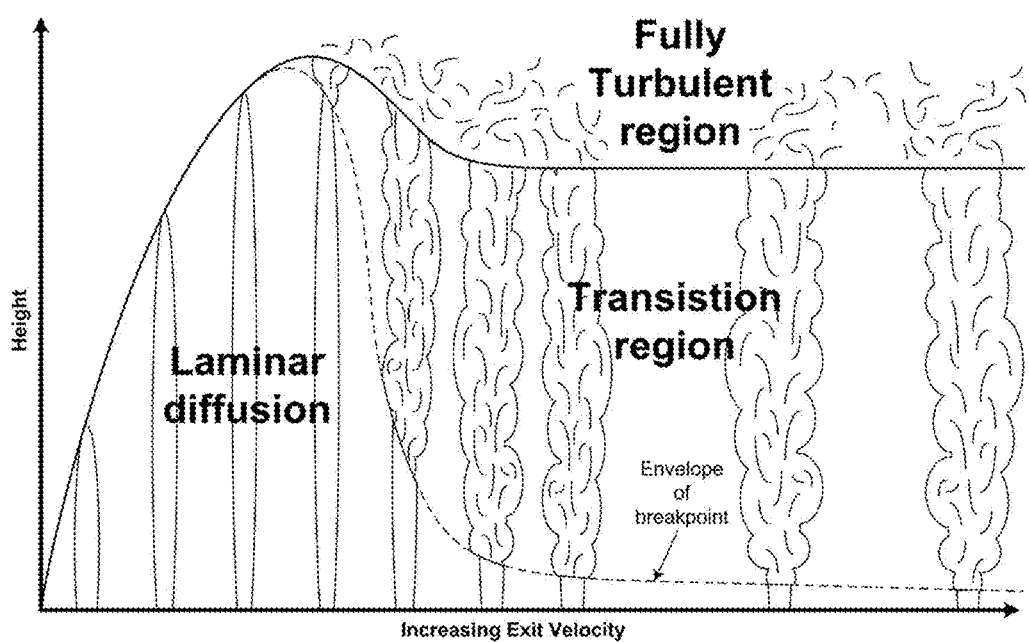
FIG. 7 depicts an exemplary graph of air flow characteristics as a function of flow height and exit velocity.

FIG. 6 provides another exemplary perspective view of an incubator as contemplated herein with primary and secondary primary air flow control devices and corresponding primary and secondary suction fans. Regarding suitable air flow, FIG. 7 exemplarily depicts a graph in which air flow behavior is shown as a function of the height of the air veil and exit velocity of air from the air flow control devices. As can be readily seen laminar flow can be achieved over a large distance at relative moderate exit velocity. Moreover, it should be noted that there is a significant transition region in which air flow is not linear but also not fully turbulent (transition region). Such transitional flow is also deemed suitable for use herein as the air flow can still be directional over a long distance. Indeed, ordered or semi-ordered air flow only breaks down at relatively long distances.

To establish a desirable air flow, the path for the internal container and the recirculation space was designed using extensive computational fluid dynamics modeling in addition to empirical testing. While the concept of an air veil works with any method which can maintain directional flow, it is typically preferred to generate a laminar flow as much as possible for the highest efficiency in environmental containment. To that end, the air veils were generated by two separate air flow control device that worked in tandem to create a guide layer which preserved the airflow boundary that separates the outside air from the conditioned air inside the incubator. Notably, using differential air velocities from the air flow control devices enabled steering of the airflow boundary to split the edge of the opening. In one exemplary configuration (as shown in FIG. 6, door in open position not shown), all outside air was forced through the recirculation space first for filtration, sanitation, and compensation. In this example, the outside (secondary) air veil had two sets of fans. The top fan employed prefiltering of ambient air with a HEPA filter and used shaped outlet ducts to help create a laminar sheet of air. The bottom (suction) fan was used to shape the airpath of the laminar flow and exhaust the collected air into the room. Thus, the secondary air veil was not subject to recirculation.

The inside (primary) air veil drew air from the recirculation space and exhausted it through shaped ducts, again forming a laminar sheet of air across the opening, bounded on one side by the laminar sheet generated by the outside air veil and by the internal container on the other side. At the end of the airpath is an opening which leads back into the recirculation space with its associated filtering and conditioning technologies via a bottom (suction) fan. It should be appreciated, however, that it is not strictly necessary to implement an external air veil, but its lack would likely result in more air exchange (due to a less than ideal airflow profile) that could be compensated for.

In the computational fluid dynamics modeling simulations (with inputs based on empirical measurements) multiple design iterations were made to examine the desirable flow characteristics. In the example of FIG. 6, the inventors determined that a desirable airflow of the air veil was in the region of 0.3 meters per second up to 0.6 meters per second, leading to laminar flow or near-laminar flow. Faster air velocities were more prone to turbulent transitional regions (which decrease overall containment efficiency by causing more mixing in the air boundary), and slower air velocities were more likely subject to the effect of external interference such as fast moving air currents (e.g. a room fan or people walking by) in the proximity of the air veils. Nevertheless, alternative airflow of the air veil may also be in the region of 0.05-0.1, or 0.1-0.2, or 0.2-0.3 meters per second or in the region of 0.6-0.7, or 0.7-0.8, or 0.8-0.9, or 0.9-1.0 meters per second, and even higher.

It should further be appreciated that the air flow in the primary air veil may be variable and regulated upon demand by specific operating modes. For example, where the door is closed, air flow may be lower than when the door is open. On the other hand, where new operating conditions are set, air flow may be increased relative to steady-state operation. Likewise, the air flow in the secondary air veil may be variable and adjusted to specific circumstances. For example, when the door is closed, no air flow may be present. Upon opening the door, airflow may be increased to the same or similar air flow as the primary air veil. On the other hand, where a hand or arm of an individual entering the opening is detected air flow in the secondary air veil may be increased to a flow rate above that of the primary air veil.

In further aspects during normal operation, contemplated incubators may minimize air currents in the internal container (similar to the eye of a hurricane). However, it should be recognized that there are occasions when rapid air exchange is desired, for example when the incubator is started for the first time. In such cases, the air current can be steered or shaped inside the internal container, either by using differential air velocities between the two veil units or by simply using vanes/nozzles to vector the air directly into the internal container.

Figure 8:
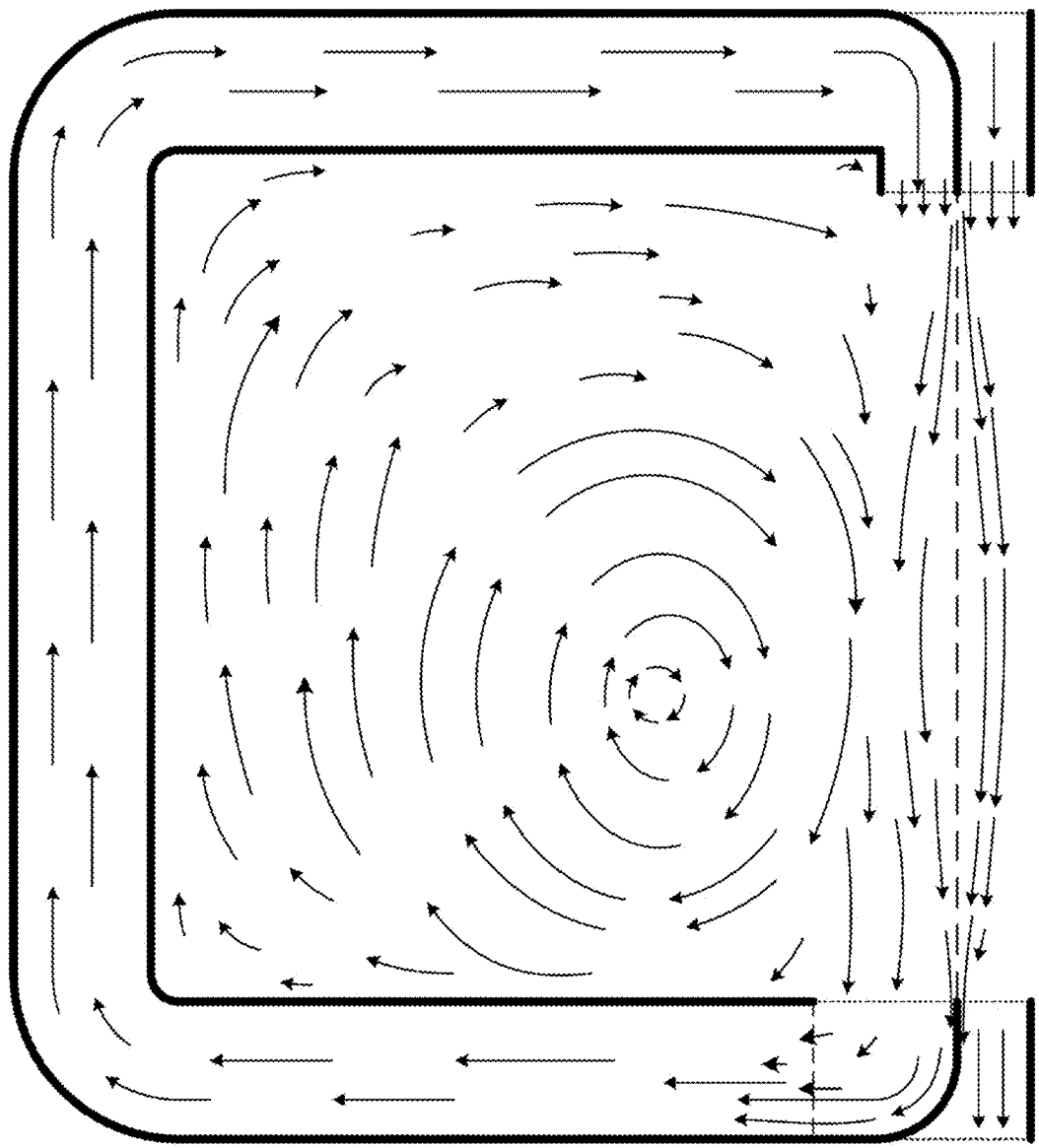
FIG. 8 depicts an exemplary view of simulated airflow using computational fluid dynamics modeling in an incubator with the internal container and recirculation space of FIG. 6 at lower air speed.
Figure 9:
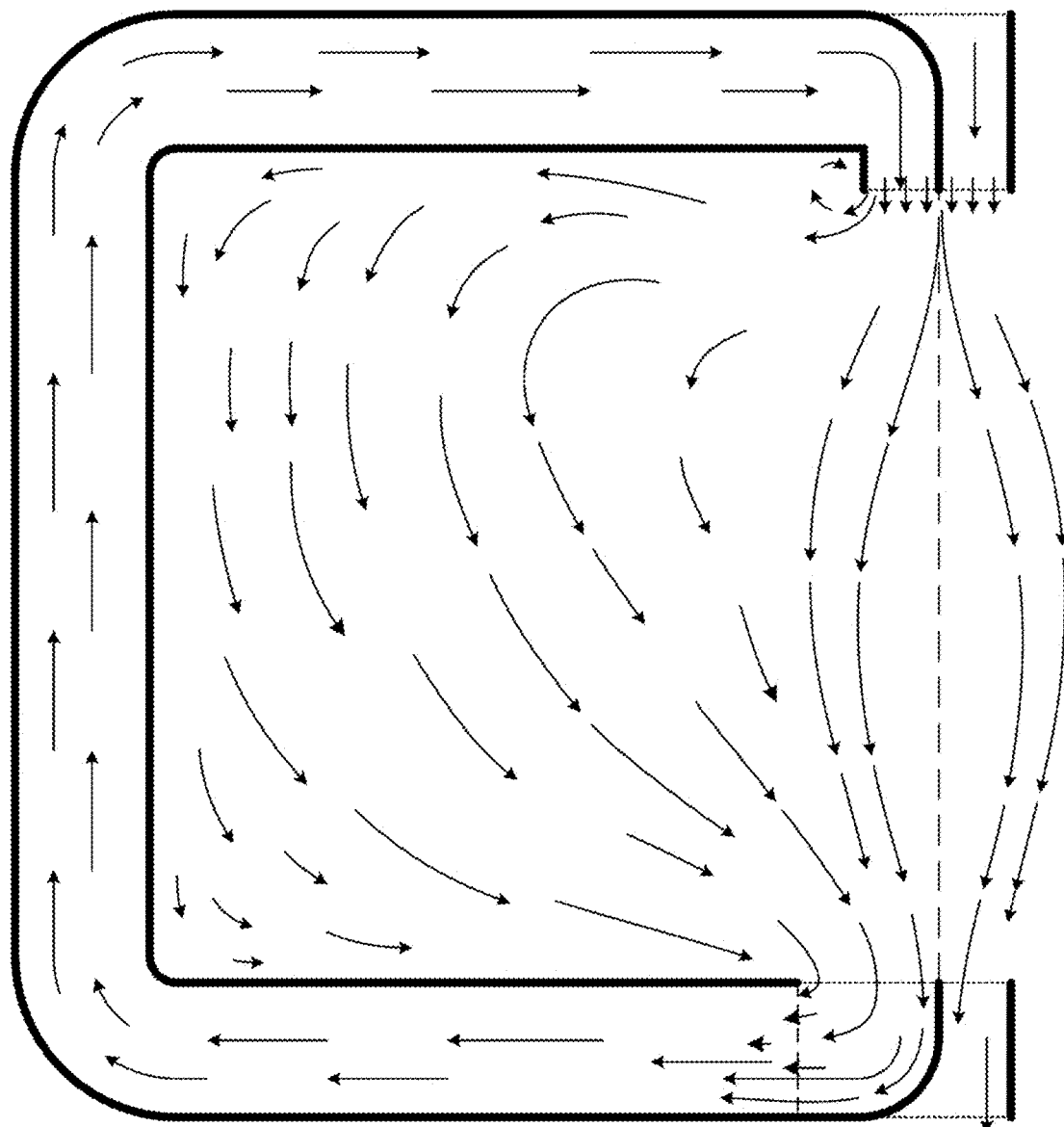
FIG. 9 depicts an exemplary view of simulated airflow using computational fluid dynamics modeling in an incubator with the internal container and recirculation space of FIG. 6 at higher air speed.
Figure 10:
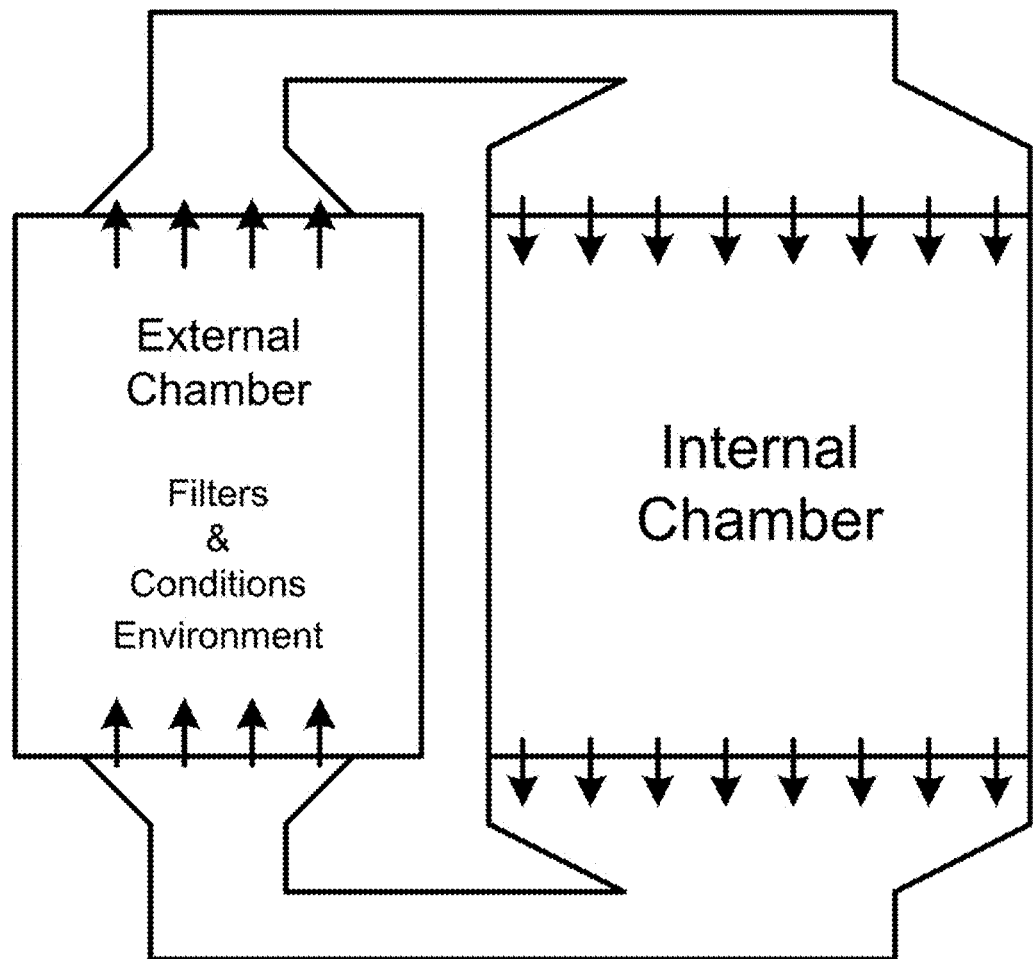
FIG. 10 depicts an exemplary view of one alternate configuration in which the internal container and the recirculation space are not coextensive.

It should also be appreciated that due to the airpath of the dual chamber design (recirculation space and internal container), fluctuations in the environmental parameters are kept in the recirculation space and be corrected before diffusing into the calmer internal container. FIG. 8 and FIG. 9 depict exemplary results from the computational fluid dynamics modeling with different air flow velocities, where the air flow in FIG. 8 was less than the air flow in FIG. 9. FIG. 10 depicts an alternate configuration in which the recirculation space is separate from the internal container, and in which adjustments in one or more environmental parameters are made within the separate external chamber that is fluidly coupled to the internal container by an entry and exit duct.

Figure 11:
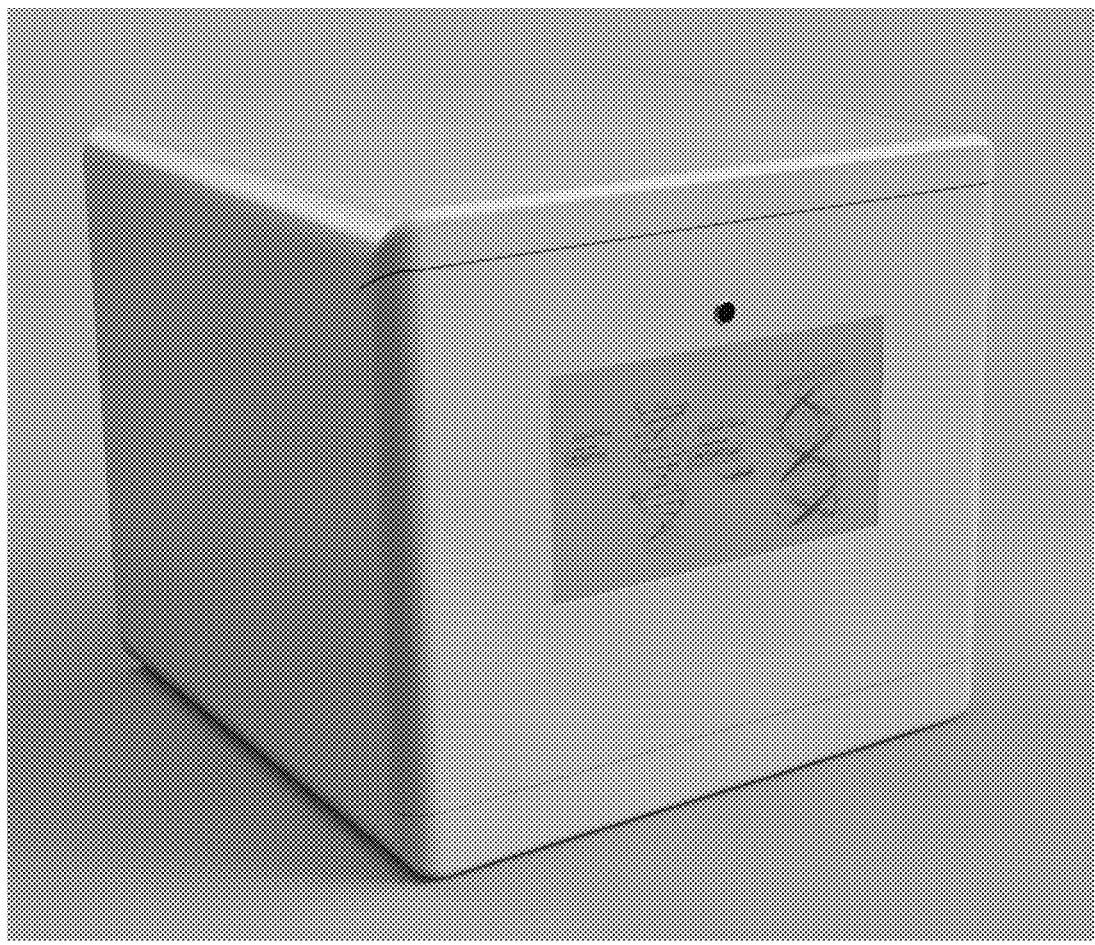
FIG. 11 depicts an exemplary view of an incubator with closed door according to the inventive subject matter.
Figure 12:
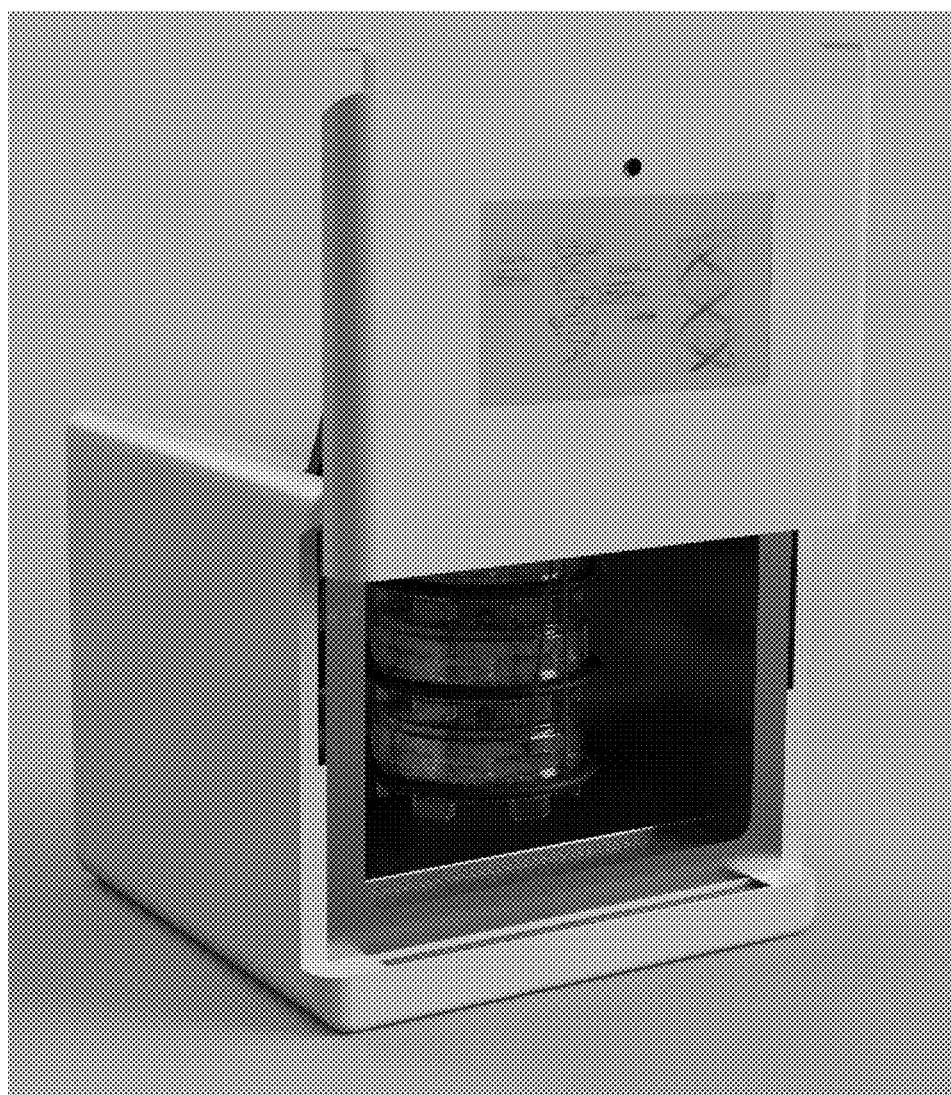
FIG. 12 depicts an exemplary view of an incubator with open door according to the inventive subject matter.
Figure 13:
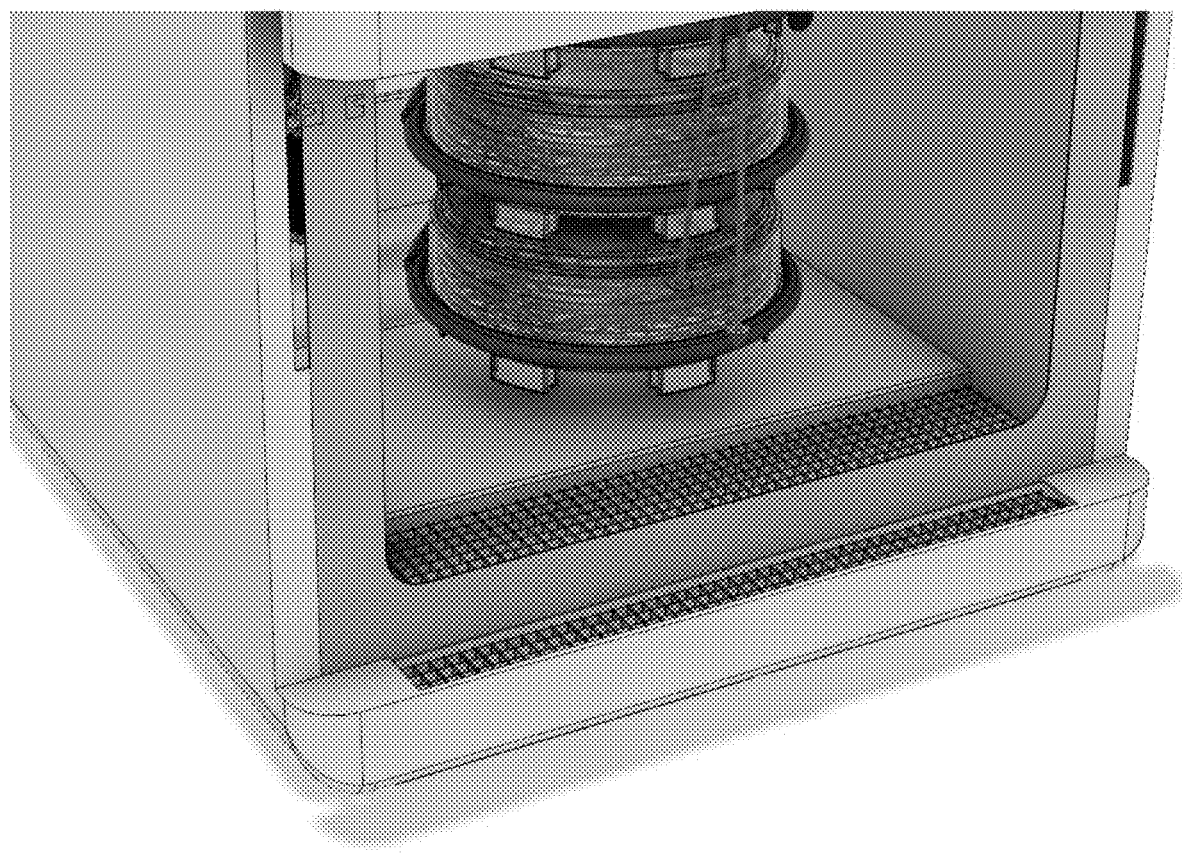
FIG. 13 depicts an exemplary detail showing air intakes for the primary and secondary suction fans.
Figure 14:
FIG. 14 depicts an exemplary detail showing primary and secondary air flow control devices.
Figure 15:
FIG. 15 depicts an exemplary perspective view of an incubator according to the inventive subject matter with cell culture containers.

FIG. 11 depicts a perspective view of an incubator according to the inventive subject matter with a screen and camera above the screen. In this example, the screen is preferably a touch sensitive screen that can accept user input, for example, to set atmospheric parameters in the incubator and/or to enter a password where access is restricted. Moreover, the screen will also typically provide further user controls (e.g., to override a programmed mode, or to modify one or more parameters) and operational status, etc. With respect to the video camera it is contemplated that the camera can use image recognition to not only authenticate specific (e.g., pre-approved) users but also to recognize gestures that correspond to specific operational controls. Of course, it should also be noted that access control may include use of a microphone and audio processing software to enable voice commands, which may be matched with image recognition. FIG. 12 shows the incubator of FIG. 11 in an open configuration, and FIG. 13 is a detail view of the incubator of FIG. 12 showing the air intake sections for the primary and secondary suction fans. FIG. 14 is another detail view of the incubator of FIG. 12 showing the open door and primary and secondary air flow control devices, along with the movable vanes. Finally, FIG. 15 depicts a perspective view of an exemplary incubator.

For example, suitable user interfaces may be part of the control unit or separate and be electronically coupled with the user interface. Among other options, contemplated user interface features include a front facing camera for facial detection and access logging. 3D scanning technology (e.g., Intel Realsense 3D) for gesture recognition for contactless control of incubator functions, and/or voice detection for simple control. In further embodiments, the incubator will have a large front panel display for fast status check and easier navigation of options. Built-in networking units may be provided so incubators can be monitored from a PC or tablet, and alerts can be set to notify a user in case of operational or other technical issues. Where desired, cloud access may be enabled to store and/or pull known ideal/working environmental conditions for various cell lines as well as facilitate researcher collaboration.

Therefore, in some preferred aspects, contemplated incubators will have a housing that at least partially encloses an internal container, wherein the internal container has an opening. A primary air flow control device is coupled to the housing and/or the internal container and directs a primary air veil along or substantially parallel to a hypothetical plane covering the opening, wherein the housing, the internal container, and the primary air flow control device are positioned relative to each other to form a recirculation space that allows for recirculation of air in the primary air veil. As noted above, the recirculation space at least partially encloses a plurality of sensors (e.g., $CO_2$ sensor, $O_2$ sensor, humidity sensor, atmospheric pressure sensor, and/or temperature sensor), and further at least partially encloses a sterilization unit, a high-efficiency particulate air (HEPA) filter, an activated charcoal filter, and/or a heater. Moreover, it is typically preferred that the recirculation space also includes one or more parts through which one or more gases (e.g., ambient air, $N_2$, $CO_2$, etc.) can be delivered to the recirculation space.

Regardless of the particular configuration, contemplated incubators will also include (or are informationally/electronically coupled to an incubator control unit that has a microprocessor and a memory storing instructions executable on the microprocessor, where the instructions cause the control unit to down-regulate the primary air flow control device and optionally cause movement of a vane coupled to the primary air flow control device upon the door moving into the second position, up-regulate the primary air flow control device and an optional secondary air flow control device upon the door moving into the first position, and/or cause movement of a vane coupled to the primary air flow control device when the door is in the first position.

Of course, the control unit will preferably also be electronically coupled to various sensors and effector circuits to maintain, regulate, and/or adjust one or more atmospheric parameters within the incubator. For example, the control unit may be electronically coupled to a temperature sensor, a gas sensor (e.g., $O_2$ sensor or a $CO_2$ sensor), an atmospheric pressure sensor, and/or a humidity sensor, and the instructions may cause the control unit to activate a heater, open a gas valve to allow entry of a gas into the incubator, and/or activate a humidifier. As will be readily appreciated, multiple redundant sensors of the same type (e.g., 3 or more) may be used to ensure continuous operation even when a single sensor fails. For example, the instructions may cause the control unit to activate the heater, to open the gas valve to allow entry of the gas into the incubator, and/or activate the humidifier when the door is being opened or is in an open position. Where desired, and as already noted above, the control unit may also be electronically coupled to an access control device that is programmed to receive a user command and/or validate an authorized user of the incubator, and wherein the instructions cause the control unit to open or close the door upon receiving the user command and/or validation of the authorized user. As will be readily appreciated, one or more functions of the control unit (e.g., door opening and closing, adjustment of operational parameters, gas flow, operation of air flow control device, and/or vane position) may also be effected by a manual, mechanical or analog control device to so provide redundancy to the system in case of a power failure or other operational downturn.

In additional aspects of the inventive subject matter, contemplated incubators may also include an atmospheric pressure sensor and/or an altimeter to allow for correct partial pressures of gases irrespective of the particular geographic location of the incubator. Moreover, even though under most circumstances contemplated incubators will operate at ambient pressure levels, it is contemplated that the incubators contemplated herein may include a pressure control unit to allow for operation at increased pressure. Where desired, suitable incubators may further include ancillary functionalities such as a red light source, one or more electronic outlets and connections, one or more wireless interfaces (e.g., to gather/transmit operational data and/or status, change operational parameters, etc.).

To further reduce excursion of atmospheric parameters within the incubator, it is also contemplated that shelfs or other moving parts may be configured to minimize the air veil. For example, a tray may be configured to include channels extending therethrough that allow flow of the air veil without generation of (or with significantly reduced) turbulent air flow. Among other options, a tray may be configured to have a honeycomb structure that permits airflow across the tray. To further facilitate servicing of and/or access to the various components, it is typically preferred that the internal container may be slidingly (e.g., via a rail or telescoping mechanism) coupled to the housing such that the housing remains stationary and that the internal container is moved away from the housing.

In still further contemplated aspects, it should be appreciated that the primary and/or secondary air veils may not only be suitable for use with an incubator as presented herein, but that the air veils may also be implemented in a glove box. Consequently, it should be noted that a glove box need no longer have a mechanically sealed environment with glove ports, but that at least a portion of the front enclosure facing an operator may be completely open but be protected by the primary and/or secondary air veils.

While contemplated incubators can be operated as most conventional incubators using one or more defined gases (such as $N_2$ and/or $CO_2$) it is further contemplated that the gases may also be provided by a separate gas supply system. Most preferably, contemplated gas supply systems will include an ambient air compressor to produce a compressed gas supply. As will be readily appreciated, the compressed ambient air will typically be subjected to cooling, dehumidification (e.g., via deep cooling, molecular sieves, adsorbents, etc.), and de-oiling where needed. Once compressed, at least a portion of the compressed ambient air is then subject to a step of air separation, preferably using a nitrogen-permissive membrane and/or pressure swing adsorption (PSA) unit to produce a product stream that is enriched in $N_2$ (typically at least 80%, or at least 85%, or at least 90%, or at least 95%, or at least 98% $N_2$). This $N_2$ enriched product stream is preferably stored in a nitrogen buffer tank from which a portion can be fed to a mixing unit. At least another portion of the compressed ambient air (containing about 21% $O_2$) can be fed to the mixing unit. Where desired, a source of $CO_2$ (e.g., having a purity at least 80%, or at least 85%, or at least 90%, or at least 95%, or at least 98% $CO_2$) may be fluidly coupled to the mixing unit. In most embodiments, the mixing unit will be configured as a manifold that can receive the compressed air, the $N_2$ enriched product stream, and the $CO_2$ product, and that has an outlet for a mixture of the compressed air, the $N_2$ enriched product stream, and the $CO_2$ product. While not needed, a dynamic or static mixer may assist in gas mixing.

Figure 16:
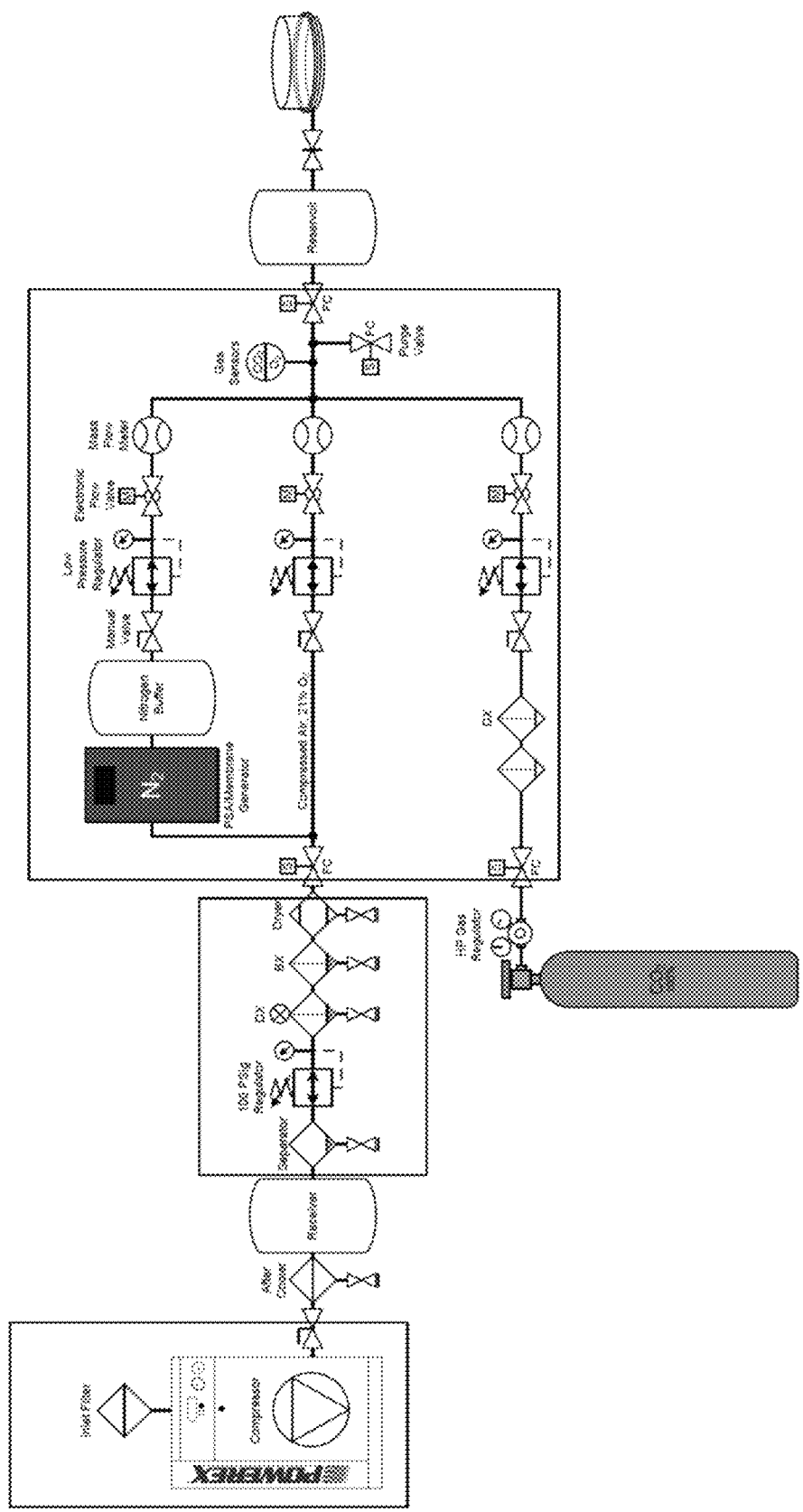
FIG. 16 an exemplary schematic for a gas supply system according to the inventive subject matter.
Figure 17:
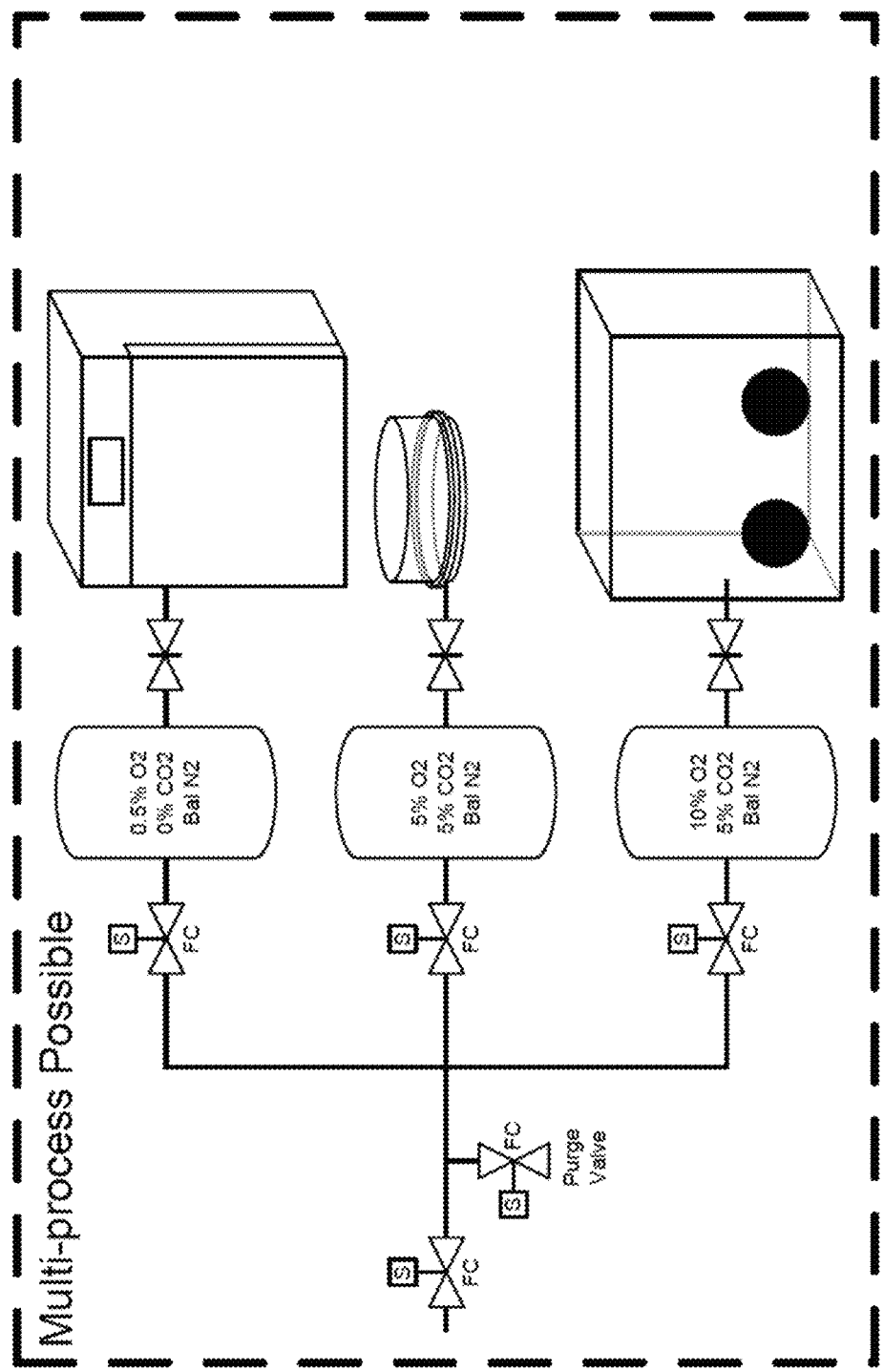
FIG. 17 depicts an exemplary schematic for a gas supply system for independent operation of multiple incubators according to the inventive subject matter.

As will be readily appreciated, each of the conduits delivering the compressed air, the $N_2$ enriched product stream, and the $CO_2$ product will typically include an electronic flow valve and a mass flow meter to ascertain precise control over the amount of gas that is to be delivered to the mixing unit. Moreover, it is also typically preferred that the conduit for the mixture leaving the mixing unit will also include one or more gas sensors (e.g., $O_2$ and a $CO_2$ sensor) that provide signals to a control unit (which may be the incubator control unit or an external control unit) to accurately control the gas composition to a predetermined set point or band. Typically, but not necessarily, the mixture leaving the mixing unit may be fed to a surge or storage tank that then delivers the gas mixture to an incubator, and an exemplary gas supply system is depicted in FIG. 16. Where multiple incubators are used with respective distinct gas compositions, each incubator may be fed from a separate surge or storage tank, all of which may be fed from the same gas supply system as is exemplarily shown in FIG. 17.

In still further contemplated aspects of the inventive subject matter it should be recognized that the incubators presented herein may advantageously use gas sources that provide raw gases or gases with less than 99-100% purity, and/or gases with less (or not exactly) defined compositions. Moreover, contemplated incubators may even receive gases with changing composition. Such is particularly beneficial as most typical incubators require the use of certified gases with known composition, which are notoriously expensive. For example, most incubators require pure nitrogen and/or pure $CO_2$, or a premixed 'trigas' supply. By placement of a set of gas sensors at the gas inlets and measuring the real-time supplied gas concentrations, valving can now be adjusted in real time as needed to maintain a desired gas mix. In this context it should be noted that most tissue culture experiments are performed with gas concentrations at ~5%-6% $CO_2$ (as a buffering agent), <0.5-20.95% $O_2$, at sea level, with the balance being $N_2$. It is therefore evident that certified high-purity (e.g., 100% concentration) gases are not absolutely required and that one can use, for example, 99.5% nitrogen or even a 95% nitrogen source (this number may vary depending cell type requirements). Consequently, the raw output of a single stage of a nitrogen generator can be used with or without a buffer tank. In still further examples, it should also be noted that the incubators presented herein can be operated as commonly known $CO_2$ incubators (and as such may not necessarily require oxygen sensors). Thus, it should be recognized that the devices and methods allow for a wide operational flexibility for use.

In still further contemplated aspects, contemplated gas supply systems will also make use of a look-up table providing correction factors for non-ideal gases such as $CO_2$, which may significantly deviate from gas behavior of $N_2$ and $O_2$ (e.g., with respect to compressibility). These correction factors can then be employed in equations to control appropriate $CO_2$ supply.

In yet further contemplated aspects, it should be appreciated that incubators as presented herein may also be set up from conventional incubators using a retrofit kit. Most typically, the incubator door of a conventional incubator in such scenario is replaced by a retrofit kit that includes a mounting frame coupled to a primary air flow control device and a primary suction fan (and optionally a secondary air flow device and secondary suction fan), wherein the recirculation is formed between the primary air flow device and primary suction fan by an external recirculation volume, for example, via suitable ducting and an optional a surge vessel. The external recirculation volume will preferably include one or more functional elements such as sensors, gas inlets, filters, etc. as described above. Finally it should be appreciated that while use of contemplated devices and methods will be especially suitable for cell and tissue culture, contemplated devices and methods are also suitable for environments where the temperature is at or below 20° C., at or below 10° C., at or below 4° C., at or below 0° C., at or below −10° C., at or below −20° C., at or below −40° C., or even lower.

Lastly, it should noted that the operational assembly (i.e., the internal container and the recirculation space) may be configured to allow removal in a single unit (e.g., assembly can be pulled out) for easy maintenance of replacement of consumables such as filters.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An incubator, comprising:
    a housing that at least partially encloses an internal container, wherein the internal container has an opening;
    a primary air flow control device coupled to the housing and/or internal container and positioned relative to the internal container to direct a primary air veil along or substantially parallel to a hypothetical plane covering the opening;
    a secondary air flow control device coupled to the housing and/or internal container and positioned relative to the internal container to direct a secondary air veil substantially parallel to the primary air veil; and
    a door coupled to the housing and/or internal container such that the entire door is movable away from the hypothetical plane and such that the entire door is moveable in a horizontal or vertical direction.

2. The incubator of claim 1 wherein the housing, the internal container, and the primary air flow control device are positioned relative to each other to form a recirculation space that allows for recirculation of air in the primary air veil.

3. The incubator of claim 2 wherein the recirculation space at least partially encloses a plurality of sensors selected from the group consisting of a $CO_2$ sensor, an $O_2$ sensor, a humidity sensor, an atmospheric pressure sensor, and temperature sensor, and further at least partially encloses a sterilization unit, a high-efficiency particulate air (HEPA) filter, an activated charcoal filter, and/or a heater.

4. The incubator of claim 1 further comprising a primary and/or secondary suction fan, wherein the primary suction fan is positioned to receive air from the primary air veil, and wherein the secondary suction fan is positioned to receive air from the secondary air veil.

5. The incubator of claim 4 wherein the secondary air flow control device is configured to receive ambient air and wherein the secondary suction fan expels the secondary air veil to the ambient air.

6. The incubator of claim 1 wherein the primary air veil and/or the secondary air veil is a directional veil or a laminar flow veil.

7. The incubator of claim 1 wherein the primary air flow control device recirculates at least 90% of all air in the primary air veil through the recirculation space.

8. The incubator of claim 1 wherein the primary air flow control device further comprises a movable vane that controls a direction of the primary air veil.

9. The incubator of claim 1 further comprising a control unit having a microprocessor and a memory storing instructions executable on the microprocessor, wherein the instructions cause the control unit to:
    a) down-regulate the primary air flow control device and optionally cause movement of a vane coupled to the primary air flow control device upon the door moving into a closed position;
    b) up-regulate the primary air flow control device and an optional secondary air flow control device upon the door moving into an open position; and/or
    c) cause movement of a vane coupled to the primary air flow control device when the door is in the open position.

10. The incubator of claim 9 wherein the control unit is further electronically coupled to a temperature sensor, a gas sensor, an atmospheric pressure sensor, and/or a humidity sensor, and wherein the instructions cause the control unit to activate a heater, open a gas valve to allow entry of a gas into the incubator, and/or activate a humidifier.

11. The incubator claim 9 wherein the control unit is further electronically coupled to an access control device that is programmed to receive a user command and/or validate an authorized user of the incubator, and wherein the instructions cause the control unit to move the door from the closed to the open position upon receiving the user command and/or validation of the authorized user.

12. The incubator of claim 11 wherein the user commend is a voice command or user gesture, and/or wherein the authorized user is validated by face recognition.

13. The incubator of claim 1 wherein the door, when in a closed position, is positioned in an area otherwise occupied by the secondary air veil.

14. The incubator of claim 1 wherein the primary and/or secondary air veil has an airflow between about 0.3 to 0.6 m/s.

15. The incubator of claim 1 wherein the internal container has a volume of between 10 and 400 L.

16. A method of operating a cell or tissue culture incubator, the incubator having a housing that at least partially encloses an internal container that has an opening, comprising:

using a primary air flow control device that is coupled to the housing and/or internal container to direct a primary air veil along or substantially parallel to a hypothetical plane covering the opening;

using a secondary air flow control device that is coupled to the housing and/or internal container to direct a secondary air veil parallel to the primary air veil; and wherein the primary and secondary air flow control devices are used when a door that is coupled to the housing and/or internal container is in an open position.

17. The method of claim 16 wherein the door is coupled to the housing and/or internal container such that the entire door is movable away from the hypothetical plane and such that the entire door is moveable in a horizontal or vertical direction.

18. The method of claim 16 wherein the housing, the internal container, and the primary air flow control device are positioned relative to each other to form a recirculation space that allows for recirculation of at least 90% of all air in the primary air veil.

19. The method of claim 18 further comprising measuring least one environmental parameter in the recirculation space using a plurality of sensors at least partially disposed in the recirculation space.

20. The method of claim 16 wherein the secondary air flow control device is not used when the door is in a closed position.

* * * * *